United States Patent [19]

Slavkin et al.

[11] Patent Number: 4,672,032

[45] Date of Patent: Jun. 9, 1987

[54] DENTAL ENAMEL PRODUCTION

[75] Inventors: Harold C. Slavkin, Beverly Hills; Malcolm L. Snead, Los Angeles, both of Calif.; Savio L. C. Woo, Houston, Tex.; Margarita Zeichner-David, Santa Monica, Calif.

[73] Assignee: University of Southern California, Los Angeles, Calif.

[21] Appl. No.: 550,527

[22] Filed: Nov. 9, 1983

[51] Int. Cl.$^4$ .................. A61K 7/16; A61K 7/18; A61K 33/42; A61K 33/16; A61K 33/06; C12P 21/00; C12P 21/02

[52] U.S. Cl. ........................ 435/68; 435/70; 435/212; 435/219; 424/49; 424/52; 424/57; 424/128; 424/151; 424/154; 530/350

[58] Field of Search .................. 435/68, 70, 172, 262, 435/317, 168, 212, 219; 424/49, 52, 57, 128, 151, 154, 177; 536/27, 28, 29; 530/350

[56] References Cited

U.S. PATENT DOCUMENTS 4,183,915  1/1980  Gaffar et al. ..................... 424/52
4,358,856 11/1982  Rubin ............................. 536/27

OTHER PUBLICATIONS

Snead et al., *J Cell Biol*, vol 95 (2pt2) 134A, Oct. 29, 1982, "Identification of a cbna Probe for Investigating Enamel Gene Expression . . . Interactions".

"Phylogenetic and Immunogenetic Aspects of Enamel Proteins", Harold C. Slavkin, et al., *Oral Immunogenetics and Tissue Transplantation* (1982), pp. 241–251.

"Enamel Extracellular Matrix: Differentiation Specific Gene Products and the Control of Their Synthesis and Accumulation During Development", Harold C. Slavkin et al., *Current Advances in Skeletogenesis*, International Congress Series No. 589, Proceedings of the Fifth Workshop on Calcified Tissues, Kiryat-Anavim, Israel (Mar. 7–11, 1982) pp. 24–33.

"Antibodies to Murine Amelogenins: Localization of Enamel Proteins During Tooth Organ Development in Vitro", Harold C. Slavkin et al. Differentiation, 23, (1982), pp. 73–82.

"Cell-Free Translation of Messenger RNAs of Embryonic Tooth Organs: Synthesis of the Major Extracellular Matrix Proteins", Victor Lee-Own, et al., *Biochemical and Biophysical Research Communications*, vol. 74, No. 3 (1977) pp. 849–856.

"Proteolytic Activity in Developing Bovine Enamel", D. Moe and H. Birkedal-Hansen, *J. Dent. Res.*, 58(B) (Mar. 1979) pp. 1012–1013.

"Isolation and Preliminary Characterization of Epithelial-Specific Messenger Ribonucleic Acids and Their Products during Embryonic Tooth Development", Margarita Zeichner-David et al., *Biochem. J.*, 185, (1980) pp. 489–496.

"Molecular Aspects of Tooth Morphogenesis and Differentiation", H. C. Slavkin, et al., *Molecular Aspects of Medicine, An Inter-Disciplinary Review Journal*, vol. 4, No. 2 (1981), pp. 125–188.

"Enamel Gene Products During Murine Amelogenesis in vivo and in vitro", H. C. Slavkin et al., *Journal of Dental Research*, vol. 61, Special Issue (Dec. 1982) pp. 1467–1471.

"Enamel-Like Antigens in Hagfish: Possible Evolutionary Significance", H. C. Slavkin et al., *Evolution*, 37(2) (1983), pp. 404–412.

*Primary Examiner*—Thomas G. Wiseman
*Assistant Examiner*—Robin L. Teskin
*Attorney, Agent, or Firm*—Nilsson, Robbins, Dalgarn, Berliner, Carson & Wurst

[57] ABSTRACT

Methods are provided for the formation of dental enamel crystals in biosynthetic matrix form by the nucleation of calcium solutions with enamel proteins and for the use of such enamel crystals as restorative material.

6 Claims, 10 Drawing Figures

DENTAL ENAMEL PRODUCTION

The United States Government has rights in this invention under the terms of NIH Grant De 02848.

FIELD OF THE INVENTION

This invention pertains to the art of dental science and more particularly to the protein chemistry and molecular biology related thereto.

BACKGROUND OF THE INVENTION

Teeth, the hard structures projecting from an anterior part of the alimentary tract and used for grasping and grinding food, vary from the chitinous projections on the radula of mollusks to the complex structures of the vertebrates. Vertebrate teeth are formed of two layers of hard materials over a living papilla, the pulp, which contains blood vessels and nerves. They form in the embryo from ingrowths of the outermost layer of the body, the ectoderm, associated with masses differentiated in the middle layer, the ectomesenchyme. The ectomesenchyme forms the dental papilla and around its outer surface, except at the end that is to remain connected with the body, lays down a layer of dentine. This material is similar to bone in composition but not in minute structure as it is harder and contains less organic matter than bone.

In human beings, beginning between the fifth and sixth months of fetal development, a layer of enamel is deposited over the dentine. Enamel is of ectodermal origin, being formed by protein secretions from ameloblasts, which are part of the enamel organ formed from an ingrowth of the epithelium of the oral ectoderm lining of the mouth. Enamel is made up of apatite and is the hardest substance produced by the animal's body, containing less than 1% organic matter. When the tooth takes its place in the jaw in the process of eruption, the enamel organ is destroyed, and no more of this substance can be produced. The enamel-producing cells in a human being (i.e. ameloblasts), are non-dividing cells, that is, they do not reproduce. The major function of ameloblasts is the production of enamel proteins, which in turn participate in the production of enamel.

Human teeth assume a fixed form. The only compensation for breakage and wear is found in the replacements that occur in the lower vertebrates. Mammals normally have no more than two sets of teeth, milk and permanent, and once the permanent teeth of adults have assumed their functional position in the jaw, loss through accident is permanent, as no new dental primordia or enamel can be formed.

The primary cause of tooth damage in humans is decay of the tooth, i.e. dental caries. Dental caries is the process in which bacteria adhere to the tooth surface, especially in pits and other harbored areas, to form plaques. Dental plaque comprises bacteria that are able to remain attached to the tooth surface because they secrete a sticky mucinous substance which is impervious to substances that might harm the bacteria. For example, water, mouthwash and saliva have little ability to penetrate the sticky mass, but fermentable carbohydrates penetrate easily. These foods are sources of energy for the dental caries-promoting bacteria.

These bacteria with their enzymes are capable of acting on fermentable foods to form acids. When sugar or carbohydrates contact dental plaque, acids are produced within a few minutes. The concentration increase continues, and by the end of a half-hour, the concentration may be sufficient to partially decalcify the tooth enamel. Decalcification stops when the acids are neutralized, until more fermentable substance is brought into the plaque, upon which the cycle is repeated. As the enamel demineralization continues, a hole or cavity is produced. When a cavity forms, the area becomes more difficult to clean and the microbes flourish.

The restoration of dental cavities through the surgical removal of decalcified enamel and the placement of dental restorative fillings is the most successful means of repairing a carious lesion. Silver amalgams, cast gold inlays, gold foil, quartz crystal composite resins and various organic polymers have served for years as effective agents for repair. Similar dental restorative materials are also used to fabricate entire teeth forms for dental replacement and/or repair. However, these artificial restorative materials are not without certain disadvantages, as are known in the art.

While the afore-mentioned dental restorative materials may produce workable dental reconstruction, metal replacement teeth and fillings tend to deteriorate, loosen or produce electrolytic action in the mouth, and organic polymers may require hazardous solvents or complicated mixing techniques. In addition, artificial repair materials tend to differ from the host structure (i.e., the natural tooth) with regard to coefficient of thermal expansion, and thus the ingestion of hot or cold foods or liquids tends to cause movement of the repair material relative to the tooth, and the eventual separation of the filling therefrom. These disadvantages result from the fact that the reconstruction materials heretofore used have artificial substances which have been used because tooth enamel is not produced by the body other than at selected times during development, and enamel production may not be selectively stimulated or produced externally. In other words, while broken bones are repaired by the body and the repair may be assisted by the proper setting of the fracture and bone growth stimulation by drugs, electricity or exercise, broken or damaged teeth may only be repaired by artificial means. It would be a substantial step forward in the art of dental science if teeth could be repaired or reconstructed with calcium hydroxyapatite crystals in a biosynthetic matrix form, i.e., natural tooth enamel. Heretofore, it has been possible to instigate crystal growth to form aprismatic matrices having various shapes and sizes. For example, calcium hydroxyapatite crystals have been grown from stable supersaturated calcium phosphate solutions by nucleation. However, it has not been possible to grow hydroxyapatite crystals in the form of dental prismatic enamel, this form being responsible for the physical properties of natural teeth.

The study of enamel proteins offers much information useful not only in basic research regarding tooth formation, but also in connection with the general aspects of craniofacial research and protein structure and function. However, such research has been limited due to the unavailability of enamel proteins in substantial quantities. Ameloblasts only produce enamel protein during a short period of time in mammals, and as the cells are non-dividing, they have not yet been cultured to produce the protein in vitro. Thus, the only method of obtaining enamel protein has been the post-mortem dissection of the forming enamel organic matrix from tooth organs of fetuses and neonates which is, of course, a limited supply. If enamel proteins were in greater supply, this problem would be overcome and basic research into the functionality and production of such proteins would be greatly accelerated. The ability to recover and synthesize the enamel protein DNA and RNA would be of great advantage in basic research and in the production of enamel protein, and the enamel protein may be used to grow apatite crystals in the form of natural dental enamel, e.g. as an advantageous dental restorative material.

The process of amelogenesis in vitro includes the biosynthesis and secretion of amelogenin and enamelin polypeptides from secretory ameloblasts upon a mineralizing dentine extracellular matrix. Both amelogenins and enamelins are glycosylated and phosphorylated. During the development of teeth when the enamel matrix is being formed, the total protein content comprises the initial enamel organic matrix. Mature enamel, in contrast to bone, has only 0.05 to 1.5% organic material on the basis of the weight of the enamel. Therefore, the biological strategy of enamel formation in vivo represents a relationship between the biochemical properties of the enamel extracellular organic matrix and subsequent biomineralization resulting in crystal nucleation, formation and growth.

Historically, enamel proteins were physically isolated on the basis of their solubility in a decalcifying solution [10% ethylenediaminetetraacetic acid (EDTA)]adjusted to pH 7.4. More recently it was shown by Termine and his colleagues *J.Biol. Chem*. 255:9760–9768 (1980)]that amelogenins were essentially soluble in guanidinium hydrochloride (4M), whereas enamelins were soluble in this dissociative solvent only with the addition of EDTA. It has been assumed that amelogenins provide a general structural constituent of the enamel matrix and also mediate the intracellular transport of amorphous calcium through the ameloblast cell for secretion to form the enamel matrix. During the transition phase from amorphous calcium phosphate to the crystallographic structure of enamel hydroxyapatite crystals [$Ca_{10}(PO_4)_6(OH)_2$ with a calcium and phosphate (Ca/P)molar ratio of 1.67], the amelogenin polypeptides decrease in size and concentration whereas the enamelin polypeptide concentration remains somewhat constant. The unique chemical and physical properties of the mature enamel, therefore, are the resultant of numerous interactions between the different enamel proteins with appropriate concentrations of inorganic ions under physiological conditions.

SUMMARY OF THE INVENTION

According to the present invention, dental caries are removed, resulting in a dental cavity, and subsequently restored with human enamel which is artifically produced in situ.

Methods are provided whereby enamel proteins are combined enzymatically with calcium and phosphate to form biological calcium hydroxyapatite crystals, i.e. tooth enamel in vitro. Methods are also provided for the use of the enamel protein to produce a human biologically active enamel in situ which may be used as a restorative material for dental caries. The enamel crystals grow in length and width until confluent with the peripheral walls or surfaces of dental cavity preparations. The result is a dental restorative material consisting of human enamel which possesses physical and chemical properties homologous with authentic human enamel.

In order to accomplish the foregoing, the invention further provides methods for the isolation of enamel proteins and enamel protein RNA and DNA sequences and for the preparation of microorganisms which produce substantial amounts of enamel proteins. Nucleotide sequences are prepared which contain the genetic information for the major constituents of human enamel extracellular matrix, the amelogenins and enamelins. The constructed gene sequences are placed within a suitable episome vector, and are amplified by replication in either infected bacterial, yeast, or selected eucaryotic cell lines. The expression of amelogenin and enamelin polypeptides and other enamel constituents (e.g. enamel peptidase, enamel protein kinase, enamel protein phosphorylase) by the infected host cell yields quantities of enamel polypeptides which maY be utilized for calcium hydroxyapatite crystal nucleation and crystal growth.

DETAILED DESCRIPTION

Figure 1:
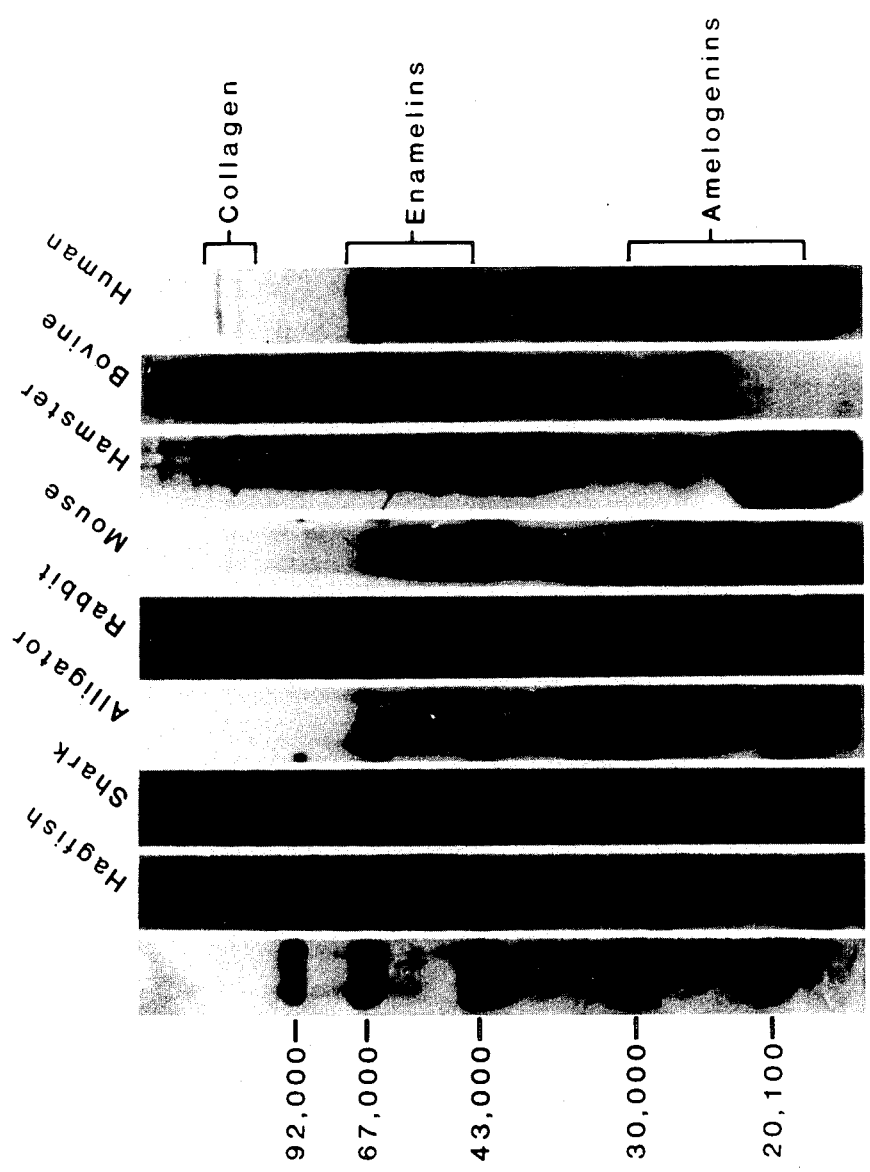
FIG. 1 shows the analysis of equivalent concentrations of various odontogenic extracellular matrices by electrophoresis in SDS/urea 10% polyacrylamide gels stained with Coomassie blue.

The procedure to fabricate enamel in vitro requires that proper proportions of enamelin:amelogenins, e.g. for human enamel a 1:10 ratio of enamelin:amelogenin, be dissolved in a solution of amorphous calcium phosphate, preferably supersaturated. A solution pH and temperature near those of the natural host are preferred. Calcium hydroxyapatite crystals may be seeded in the reaction mixture to enhance the nucleation of crystal formation. Alkaline phosphatases and/or proteolytic enzymes, e.g. serine esterases or proteases, may also be added to the solution to aid in the formation of restorative enamel which is homologous to the naturally occurring dental enamel. Proteolysis during enamel matrix formation has been suggested upon the discovery of a neutral or slightly alkaline protease which appears to have specificity for fetal bovine enamel proteins (i.e. amelogenins) [Moe, D., and Birkedal-Hansen, *J. Dent. Res.* 58(B): 1012—1012 (1979)]. The optimal protease activity with fetal amelogenins occurs with a serine esterase at a pH 7.2–8.1 at 37° C.

To render the most effective oral health service to the patient, it is imperative that a comprehensive diagnosis be made prior to the institution of any treatment. After a general survey of the entire oral cavity, a critical examination is made for dental caries and other diseases and/or abnormalities of teeth and their supporting structures. In diseased teeth, not only must dental caries be removed, but the integrity of the adjacent sound dental tissues must be conserved and safeguarded. This is accomplished by a critical diagnosis of the lesion, appropriate development of a treatment plan, and careful attention to the anatomy, tooth crown morphology, shape and size of embrasures, and position and shape of the contact areas between teeth. Such dental procedures, as known in the art, must be based upon thorough diagnosis, proper treatment planning, and the technical expertise required to restore a diseased region or regions of one or more teeth.

In order to describe the technical procedures associated with this invention, the example is offered of an occlusal class I preparation and the methods for restoring human enamel. It is essential to note that all previous methods for occlusal class I preparations and procedures for restoration are based upon the essential physical and chemical properties of the restorative material. For example, occlusal class I preparations for cast gold restorations were designed to complement the properties of a cast gold material; the same is true for silver amalgam, porcelain, gold foil, or plastic filling restorations. In contrast, the indication for human enamel as a restorative medium in the occlusal surfaces of posterior teeth, for example, does not depend upon the physical-chemical properties of human enamel material. This restorative material bonds to the existing enamel tooth structure without cement or artificial mechanical-designed retention features in the cavity design.

The fundamental principle of cavity design for occlusal class I cavities which are to be filled with human enamel on the occlusal surfaces of bicuspid and molar teeth require the complete removal of all dental caries. It is assumed that the carious lesion does not extend into the tooth structure beyond the enamel/dentine junction; the lesion is localized in the enamel structure per se. The outline of the cavity should encompass the lesion and extend only as far as needed to provide areas for proper finishing and polishing of the completed restoration. The depth of the cavity should extend only as deep as required to completely remove the dental decay (e.g. to the enamel/dentine junction) and the mesial, distal, buccal and lingual walls of the prepared cavity should be parallel to the long axis of the enamel rods found in this anatomical position. No resistance or retention lines or point angles are required since the restorative enamel will interlock and bond to the enamel prisms of the adjacent enamel structure. The cavity shaping procedures can readily be accomplished using conventional rotary dental burrs which are fissured to enhance the removal of dental caries and a number of spoon-shaped dental instruments can also be used.

Following the mechanical removal of all dental caries, and the thorough cleansing of the cavity region, the cavity is prepared and ready to receive the human enamel restoration. As opposed to artificial restorative materials, the restorative human dental enamel of the present invention is not inserted into the cavity, but rather forms or is 'grown" in the cavity preparation. It should be noted that the isolation of the tooth, the instruments and techniques used to remove dental caries and shape the cavity, the solutions to sterilize the cavity, and other required methods are according to procedures known in the art and science of operative dentistry and may be employed or performed without undue experimentation.

In a procedure to grow human dental enamel within the occlusal class I cavity preparation, 1:10 proportions of the enamelin/amelogeninens (produced as will be described) are dissolved in a supersaturated solution of amorphous calcium phosphate containing 10 ppm fluoride, preferably in the form of sodium fluoride, stannous fluoride or stannous hexafluorozirconate, as human and animal enamel containing calcium fluoroapatite crystals has been found to be more resistant to dental caries. The solution preferably has a pH of 7.4, and a temperature of 37.5° C. A volume of about 0.5 ml is sufficient for the restoration of the described cavity preparations. Calcium fluoroapatite crystals (0.1%) may be added to the reaction mixture as catalyst to enhance the nucleation of crystalite formation as mediated by the two classes of enamel proteins. The reaction mixture also contains 0.1% serine esterase enzyme to degrade the enamel proteins. Following the completion of enamel crystal formation, occlusal restorative material may be finished with assorted finishing burrs, discs and wheel-shaped armamentaria, as is known in the art, to eliminate excess enamel.

The finished enamel dental restoration embodies all the requirements of physiologic tooth form, structure and function. To accomplish this, all contours, embrasures and marginal ridge relationships, size, shape and position of contact areas, and all occlusal anatomy are developed in the enamel dental restoration. The restorative enamel growth replicates the direction of natural enamel prism shapes and forms, and the restorative enamel will grow and develop in juxtaposition to endogenous enamel prisms and rods of the tooth structure.

The proteins which produce the homologous dental enamel have been divided into two major classes according to their physico-chemical properties: enamelins and amelogenins. The enamelins are acidic glycoproteins with molecular weights ranging from about 58 to 72 kilodaltons (kd). They are rich in the amino acids glutamic acid, aspartic acid, glycine and serire, and have a very high affinity for hydroxyapatite, therefore requiring demineralization procedures for their extraction. The amelogenins are hydrophobic proteins, enriched in the amino acids proline, glutamic acid, histidine and leucine, and easily solubilized in most solutions, with molecular weights in the ranges of about 22 to 30 kd.

Specific polyclonal antibodies against the specific proteins (i.e. enamelins and amelogenins) are used to identify the messenger ribonucleic acids for these proteins; to identify the clones containing cDNA for enamelins or amelogenins; and to detect the expression of these proteins in the newly-created organisms. Four kinds of such antibodies have been produced: 1) polyclonal antibodies against all the proteins present in the enamel organ epithelia and the dentine and enamel extracellular matrices; 2) polyclonal antibodies against purified mouse amelogenins; 3) polyclonal antibodies against purified rabbit enamelins; and 4) polyclonal antibodies against isolated human enamelins. These antibodies have been shown to be immunologically cross-reactive with all vertebrate species studied Enamel organ epithelia from selected vertebrates are used as a source of total nucleic acids and the messenger ribonucleic acids (mRNA's) isolated therefrom. The mRNA's are isolated from the other nucleic acids by affinity chromatography, and their translational activity determined in a cell-free system. The enamelin and amelogenin mRNA's are identified by immuno-precipitation of their translation products with their respective specific antibodies.

Cells (i.e. bacteria, yeast or eucaryotic cells) are then created which contain in their genome a cDNA or a genomic DNA fragment for a specific enamelin, amelogenin or any other enamel protein. We describe how to produce a cDNA library containing mRNA sequences for all the mRNA's present in the enamel organ epithelia; how to convert the original single-stranded cDNA (SS-cDNA) into a double-stranded DNA (ds-cDNA) ready for insertion into a vector; and how to attach the ds-cDNA to the vector DNA and subsequently its introduction into a bacterial, yeast or eucaryotic cell for its transcription.

Procedures are described to facilitate transcription of the enamel proteins into bacteria, yeast and eucaryotic cells, and immunological methods are provided to detect the presence of enamel proteins in the cells or the surrounding media, as well as biochemical characterization of the new proteins synthesized by their physicochemical properties previously described.

Poly(A)-containing mRNA sequences are used for the synthesis and cloning of enamel protein cDNA, which may be produced in a single- or double-stranded form. The double-stranded cDNA is then inserted into bacterial, yeast or eucaryotic cell lines which then contain in their genome the genes for the proteins that contribute to the extracellular enamel matrix. Alternatively, the single-stranded cDNA may be employed to screen a human gene library for the genomic DNA sequences which contain the enamel structural genes which include the intervening sequences which insure optimal expression of human gene products. These DNA genomic fragments are then joined to a vector and transfected into a host cell, which may then be amplified to produce enamel proteins homologous to those biosynthesized in vivo.

The preferred microorganism for the production of amelogenin and enamelin polypeptides for use in the formation of artificial human enamel crystals is yeast, and specifically, *Saccharomyces cerevisiae* (Baker's Yeast) which is superior to bacteria in several ways. Yeast tends to grow very well in artificial environments and produce a very high yield. In addition, yeast contains a group of enzymes that allow for the posttranslational modification of the gene product. For example, yeast adds sugars and phosphates to the nascent enamel polypeptides in a manner which is nearly identical to the modifications that occur in the human cell, thus producing the glycosylated enamelins and the glycosylated and phosphorylated amelogenins of natural tooth enamel which have been heretofore described. While such proteins may be produced by bacteria or other microorganisms, further recombinant modifications of the genome would be required to produce such functional proteins, which appear to be indistinguishable from the proteins produced by natural human enamel cells.

Relatively few genes from multicellular creatures have been expressed in *E. coli*, possibly due to the differences between procaryotes and eucaryotes regarding transcription, translation and post-translational processing. Yeast cells, being eucaryotes, possess suitable metabolic machinery to regulate the fidelity of higher eucaryotic gene expression. The *Saccharomyces cerevisiae* cells are transformed by incubation with reducing agents (e.g. dithrothreitol), digestion of cell wall polysaccharides and extensive washing in sorbitol to produce yeast spheroplasts which will uptake foreign DNA in the presence of calcium chloride and polyethylene glycol. The spheroplasts are then embedded in a solid matrix of 3% agar to facilitate the regeneration of the yeast cell wall. Within two-seven days, the transformed yeast colonies grow and thus amplify the number of cells containing the human enamel genes. Enamel gene expression is monitored using a number of detection assays including immunochemical procedures designed to detect nanogram, picogram and fanogram yields of human enamel gene products. A number of modifications which increase the yield of enamelins and amelogenins from the transformed yeast colonies will be apparent to one skilled in the art without undue experimentation and without departing from the purview of the present invention.

From these transformed yeast colonies, enamelins and amelogenins are physically isolated from the nutrient medium using gel exclusion chromatography to separate the major enamelins (approximately 62–72 kd) from the major amelogenins (ranging from 30–20 kd). Isolated and purified enamel proteins are lyophilized and stored until required.

The following examples will describe in detail the formation of the proteins which produce the described homologous dental enamel, according to the following outline.

I. Identification of the Major Enamel Proteins
  A. Identification of Rabbit Enamel Protein
  B. Identification of Murine Enamel Protein
II. Production of Polyclonal Antibodies Against Enamel Proteins
III. Isolation of Enamel Protein mRNA
IV. Production of Enamel Protein DNA Lineages
  A. Isolation of Enamel Organ Epithelial Specific mRNA and Cloning of its Complementary DNA
  B. Identification and Isolation of Clones Containing Enamel Specific DNA Sequences by Nucleic Acid Hybridization
    1. Colony Hybridization
    2. Bi-Directional Southern Blots
    3. Hybrid Selected Translation and Immunoprecipitation
    4. DNA Sequencing
    5. Characterization of Enamel Gene Clones by Restriction Endonuclease Digestion
  C. Identification of Enamel Genes from Gene Libraries
V. Production of Transformed Cells Which Express Enamel Gene Products
  A. Expression in Bacteria
  B. Expression in Yeast
  C. Transformation and Expression in Eucaryotic Cells D. Identification by Immunologic Determinants
1. Preparation of Agar on Agarose Plates Containing the Specific Antibodies
2. $^{125}$I-Labeled Antibody Assays
3. Immunoassay of Cell Protein Extract Example I Identification of the Major Enamel Proteins Several methods for the extraction of enamel proteins were analyzed: 1) demineralization and extraction with 0.5M acetic acid at 4° C.; 2) demineralization in 5% cold trichloroacetic acid followed by extraction with 6M urea in 200 mM Tris-borate buffer, pH 8.6; 3) extraction in homogenization buffer (125 mM Tris-HCl, pH 6.8; 2% SDS; 5% 2-mercaptoethanol and 250 mM sucrose) by boiling for 5 minutes; and 4) sequential extraction in 4M guanidine-HCl, pH 7.4 followed by extraction in 4M guanidine-HCl/0.5M EDTA, pH 7.4. Comparison of the extracted proteins by electrophoresis in SDS/urea 10% polyacrylamide gels showed that each extraction method provided useful yields of the same enamel proteins. Several differences were found for each method which could be used to advantage. For example, homogenization buffer is a fast extraction method and is very useful for $^{35}$S-methionine metabolic labeling of tooth organ cultures. Acetic acid and guanidine-HCl extraction methods produce higher yields of enamel proteins. Acetic acid extraction results in an enrichment of rabbit fetal enamelins (approximately 40% of the total extracts) and of mouse neonatal amelogenins (60% of the total extract). Sequential extraction with guanidine-HCl is the best method for protein extraction from shark teeth. The shark enameloid contains a very high concentration of collagen mixed with the enamel and there is no distinguishable enamel/dentine junction. Shark tooth collagen is completely removed in the first extraction with guanidine-HCl, while enamelins are extracted and enriched in the guanidine-/EDTA extraction.

Comparisons between several species of vertebrate enamel matrix proteins, shows that the family of enamel proteins consists of a class of proteins of approximately 58–72 kd (equivalent to the enamelins), and a second class of approximately 22–28 kd corresponding to the amelogenins. FIG. 1 shows a comparison of enameloid and enamel matrix proteins from a number of aquatic and terrestrial vertebrates. Both class members of the enamel protein family are present in mouse, hamster, porcine, bovine and human, but marked differences are observed such as relative concentration depending on vertebrate species, developmental stage and enamel maturation. For example, rabbit enamel matrix is rich in enamelins and does not contain amelogenins. Mouse enamel matrix, however, is rich in amelogenins (>90% of total matrix protein) and also contains a 62 kd enamelin ( 5%). In contrast, shark enameloid contains only enamelins (approximately 55 kd molecular weight). The enamel proteins from the tooth organs of the hagfish (Eptatretus stoutii), hammerhead shark, alligator (Alligator mississippiensis), hamster (Cricetus auratus), sheep (Ovis aries), cow (Bos taurus), pig (Sue scrofa), monkey (Macaca mulatta) and human (Homo sapiens) have been isolated, and the amino acid compositions thereof determined, by similar methods. The amino acid composition of enamel proteins from the selected vertebrates are shown in Table I. For convenience, all tables described herein are set forth at the end of the specification.

A. Identification of Rabbit Enamel Protein

Figure 2:
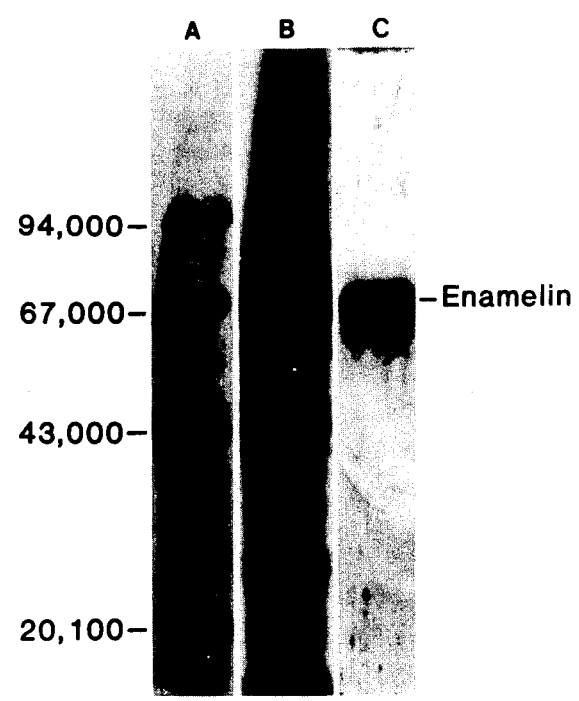
FIG. 2 depicts the SDS/urea 10% polyacrylamide gel electrophoresis of proteins from rabbit molar and incisor extracellular matrices extracted in 0.5N acetic acid (lane A, molecular weight markers, lare B, total protein distribution and lane C, purified rabbit enamelin)

To determine the major proteins which characterize the ameloblast phenotype, 25- and 26-days gestation fetal New Zealand White rabbit molar tooth organs were isolated and mechanically separated into enamel organ epithelia with adjacent enamel extracellular matrix (EOE) and dental papilla mesenchyme. In replicate studies, EOE preparations were sonicated to remove cells, resulting in an extracellular matrix preparation (EM). Fetal enamel proteins were extracted using either 0.5M acetic acid, SDS-MET-containing buffer, or sequential dissociative methods with guanidine-EDTA solution. Extracts from each preparation were electrophoretically separated on polyacrylamide gels in the presence of SDS and urea. The major fetal rabbit enamel protein has a molecular weight of c. 70 kd, as is shown in FIG. 2. This protein was isolated from the gel and identified as enamelin by its amino acid composition (Table II). Approximately 40% of the total proteins extracted is the 70 kd enamelin.

B. Identification of Murine Enamel Protein

Figure 3:
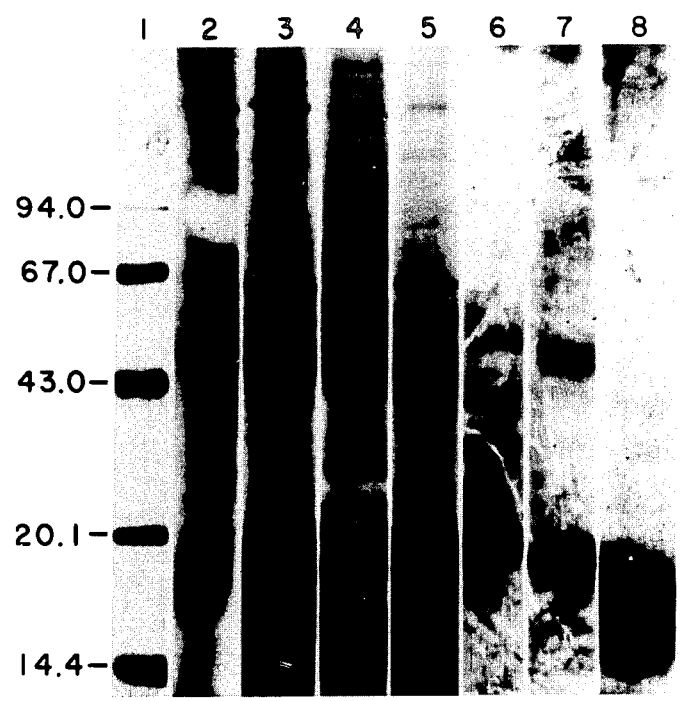
FIG. 3 shows the SDS-polyacrylamide gel electrophoresis of murine amelogenin polypeptides.

To determine the major proteins which characterize the murine ameloblasts phenotype, 5-day postnatal Swiss Webster strain tooth organs were isolated and mechanically separated into enamel organ epithelia with adjacent extracellular matrix (EOE) and dental papilla mesenchymes. In separate experiments, EOE preparations were sonicated to remove cells, resulting in an acellular extracellular matrix (EM). Mouse enamel proteins are readily extracted using either 0.5M acetic acid, SDS- MET-containing buffer, or guanidinium-EDTA solution. Extracts from each type of preparation were resolved with electrophoresis on SDS/urea-polyacrylamide gels. SDS-polyacrylamide gel electrophoresis of polypeptides of amelogenin-enriched fractions which were isolated using different extraction procedures, purified amelogenin bands were excised, and the proteins were eluted and re-electrophoresed. In FIG. 3, lane (1) shows molecular weight markers: phosphorylase B (94 kd), albumin (67 kd), ovalbumin (43 kd), soybean trypsin inhibitor (20 kd) and lysozyme (14.4 Kd). Lane (2) shows enamel organ epithelium with extracellular matrix (EOE) polypeptides extracted with sequential guanidine-EDTA. Lane (3) shows EOE polypeptides extracted with SDS-mercaptoethanol containing buffer. Lane (4) shows EOE polypeptides extracted with 0.5M acetic acid and (5) is amelogeninenriched extraction from isolated extracellular matrix using acetic acid. Lane (6) shows amelogerin bands containing the eluted and re-electrophoresed 28 kd polypeptides. Lane (7) shows 26 kd polypeptides which were eluted and re-electrophoresed. Lane (8) shows the eluted and re-electrophoresed 22 kd amelogenin polypeptides.

The major enamel proteins extracted from postnatal incisors and molars are a family of related polypeptides: 28, 26 and 22 kd (amelogenins) which represented approximately 60% of the total acetic acid extractable proteins. These proteins were isolated from the gels and characterized as amelogenins by their typical amino acid composition (Table III).

Partial amino acid sequence of the first thirty amino acids of the amino-terminal region of the mouse 26 kd amelogenin was identical to the sequence reported for amelogenins obtained from pig, cow and human, thus indicating their conservation in different mammalian species (Table IV).

Example II

Production of Polyclonal Antibodies Against Enamel Proteins

Antibodies were prepared against purified proteins: (1) mouse amelogenins (c. 20 kd), (2) rabbit enamelins (c. 70 kd) and (3) human enamelins (c. 62 kd). Using young female New Zealand White rabbits, high titers of polyclonal antibodies against mouse, rabbit and human enamel proteins have been produced. The rabbits produced antibodies against their own enamel. Purified proteins were obtained by fractionation on SDS/urea 10% polyacrylamide gel electrophoresis, specific bands were cut, neutralized, homogenized and emulsified in complete Freund's adjuvant. Rabbits were immunized and the antisera characterized by indirect immunofluorescence, immunoprecipitation, ELISA and micro-ELISA assays, and dot-immunobinding assay.

The immunofluorescent reaction was positive for ameloblasts, as well as newly secreted extracellular enamel matrix. A positive reaction was noted, albeit very lightly, associated with stratum intermedium cells adjacent to the secretory ameloblasts. Epidermis, hair follicles, salivary glands, mammary glands, cartilage, bone, brain, spleen and liver were all negative. Absorption of the rabbit anti-mouse enamel protein IgG fraction with immunogen served as a negative control and removed all positive fluorescent staining. The enamel protein antibodies were immunologically crossreactive with vertebrate enamel matrix constituents as determined by indirect immunofluorescence, ELISA, micro-ELISA and dot-immunobinding assays.

Figure 4:
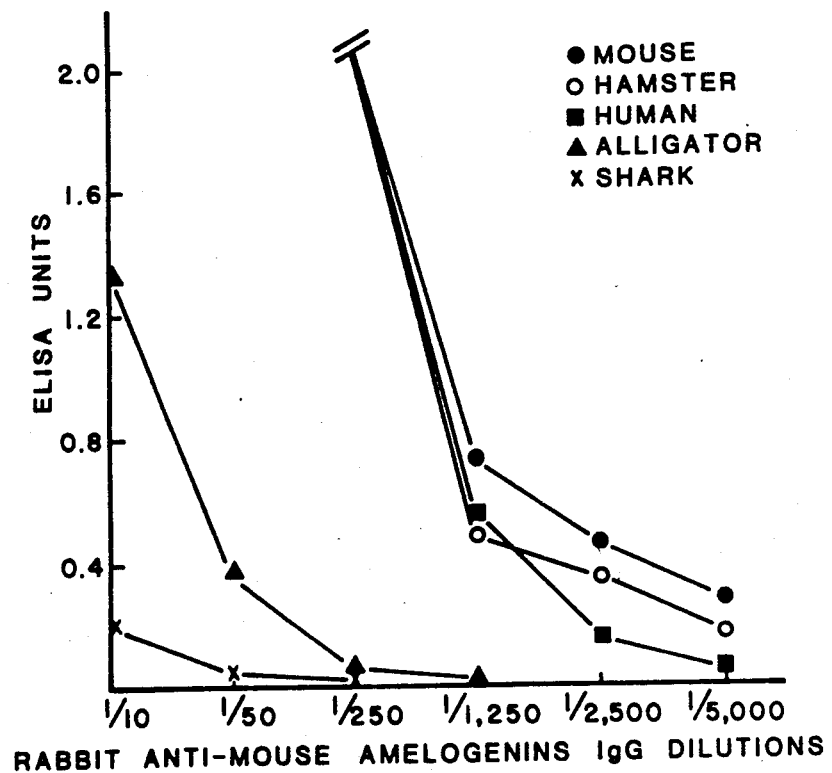
FIG. 4 is an ELISA dilution curve using rabbit antimouse amelogenin 1 gG dilutions.

Polyclonal antibodies directed against either purified enamelins or amelogenins are immunologically crossreactive with lower and higher vertebrate enamel proteins by a number of different criteria including immunodetection assays sensitive in the nanogram range. For example, the dot-immunobinding assay is a simple and sensitive procedure which has been used to characterize a 1:100 dilution of either enamelin or amelogenin IgG antibody fractions using 1–250 ng of antigen: controls included 1–250 ng of type I collagen, albumin, and soybean trypsin inhibitor. Positive antigens included enamel proteins isolated and purified from hagfish, shark, alligator, mouse, rabbit, hamster and human species. Whereas chemical evidence suggests that enamelins and amelogenins are two different classes of enamel proteins, immunological data indicates that each type of enamel macromolecule shares antigenic sites within the protein. The specific source of the enamel protein antigenicity is not yet known. What is of significant advantage, however, is the application of these polyclonal antibodies to identify the translation products of enamel mRNA's using a reticulocyte cell-free system. FIG. 4 shows an ELISA dilution curve using rabbit anti-mouse amelogenin IgG dilutions for proteins isolated and purified from mouse, hamster, human, alligator and shark tooth organs as described.

Example III

Isolation of Enamel Protein mRNA

Enamel protein messenger RNA was obtained from mouse and rabbit isolated enamel organ epithelia. The total RNA extracted was separated into poly(A)containing RNA (mRNA's) and non-poly(A)-containing RNA (rRNA and tRNA) by chromatography on oligo(dT)-cellulose. The presence of mRNA molecules during the process of purification was monitored by their translational activity in a reticulocyte lysate cell-free system.

From approximately 1,600 molar organs dissected from 25-day old New Zealand White rabbit fetuses or 5-day post-natal Swiss Webster mice, the RNA was extracted by the proteinase-K method described by Rowe et al, *Biochemistry* 17, 1581–1590 (1978). For each 1 g of frozen organ, 10 ml of the following buffer was added: 10 mM-Tris/HCl, pH 7.5, 1% SDS, 5 mM-EDTA, 65 μg of proteinase K/ml. The samples were homogenized at room temperature and incubated for 1 hour at 37° C. The homogenate was adjusted to 1% Triton X-100, 1% sodium deoxycholate, 0.1M NaCl and 0.5 mg of heparin/ml. The RNA was extracted three times with phenol/chloroform (1:1, v/v), precipitated and washed several times with ethanol. The concentration of RNA was measured by the $A_{260}$ of the aqueous RNA solution by assuming that $1A_{260}$ unit=50 μg of RNA. The RNA was kept precipitated at −20° C. until use.

In order to isolate the poly(A)-containing RNA, the total RNA was passed through an oligo(dT)cellulose column as described by Aviv et al, *Proc. Natl. Acad. Sci. U.S.A.* 69, 1408–1412 (1972). Each of the RNA fractions eluted from the column was precipitated and washed with ethanol and kept at −20° C. until further utilized.

The fractionation of poly(A)-containing RNA was accomplished by ultracentrifugation on sucrose gradients containing 50% (v/v) formamide. Linear gradients from 5 to 20% (w/v) sucrose in 0.1 MLiCl/0.05 M EDTA/0.2% SDS/0.01 M Tris/HCl, pH 7.4, were loaded with 350 μg of heat-denatured RNA/ml. The gradients were centrifuged at 25° C. for 16 hours at 30,000 rev./min. Fractions (0.4 ml) were collected and the $A_{254}$ was continuously monitored. The fractions were precipitated with ethanol, washed several times with 0.4M NaCl/66% (v/v) ethanol to eliminate the formamide, and kept at −80° C.

An average yield of 5–6 mg of total RNA was obtained from approximately 1,600 molar organs. Of the total RNA, 6% was bound to the oligo(dT) cellulose.

In the example of the rabbit, the poly(A)containing RNA species (i.e. 6% of the total RNA), were fractionated according to sedimentation coefficients by ultracentrifugation in sucrose gradients, and the mRNA fraction sedimenting in the 16-26S region was pooled and tested for its translational activity in the cell-free system.

The cell-free system used was the rabbit reticulocyte-lysate 'Translation Kit' prepared by New England Nuclear Corp., Boston, MA, U.S.A., with [$^{35}$S]methionine. The method described by the suppliers was followed. The reactions were carried in 25 μl assay mixtures containing 22 Ci of [$^{35}$S]methionine, 2 mM-magnesium acetate, 80 mM-potassium acetate and 1–10 μg of RNA. The samples were incubated for 1 hour at 37° C. Samples (1 μl) were taken to determine the radioactivity incorporated by placing them on a glass-fibre filter, followed by precipitation with cold 10% (v/v) trichloroacetic acid. After several washes with trichloroacetic acid, the filters were boiled for 10 minutes, cooled, washed again with 5% trichloroacetic acid, rinsed with ethanol and air-dried. The filters were counted for radioactivity by liquid scintillation spectrometry after the addition of 5 ml of Aquasol. The rest of the sample was treated with an equal volume of polyacrylamide-gel sample buffer, reduced with mercaptoethanol, heat-denatured at 70° C. for 15 minutes and analyzed by polyacrylamide-gel electrophoresis and fluorography.

The results showed that the reticulocytelysate cell-free system alone, with no exogenous mRNA added, synthesized two proteins. Their molecular weights were determined as 49 and 19 kd respectively. In the presence of a 16–26S rabbit mRNA fraction, in addition to these proteins, two distinctively different proteins of higher molecular weight were also present. These two proteins have molecular weights of 65 and 58 kd, respectively. Also, the protein band of 49 kd was broader than that present in the control, indicating the possibility of another protein being synthesized in the presence of the exogenous mRNA which migrates in the same position. These results clearly indicate that the 65 and 58 kd proteins synthesized in the presence of a 16–26S mRNA are enamel proteins. Further characterization by agarose gel electrophoresis indicated that rabbit enamelin mRNA's have a sedimentation coefficient of 19–20S.

To establish an identity between the proteins synthesized in the cell-free translation of the isolated mRNA species and the proteins that were synthesized by the enamel organ epithelium in organ culture, the fluorography profiles obtained for each one were compared. All three proteins synthesized in the cell-free system correspond by molecular weight to an equivalent protein synthesized by the original tissue. The 19–20S mRNA fraction contains the coding information for two enamelins, representing specific ameloblast gene products of 65 and 58 kd.

We have investigated enamel mRNA's at different stages of fetal through postnatal rabbit tooth development. RNA's were isolated from 21-days gestation rabbit molar tooth organs through 2-days postnatal age. Extracted RNA's were purified and tested for translational activity using the reticulocyte-lysate cell-free system. The earliest enamelin mRNA activity was detected at 23 days gestation, reached a maximum at 24–25 days gestation, and disappeared at approximately 28–29 days fetal rabbit molar development. These results show that the transcription activity of enamelin mRNA's is closely coupled to the de novo translation of enamel proteins (i.e. enamelins). Both translation products were immunoprecipitated with enamelin or amelogenin antibodies.

Figure 5:
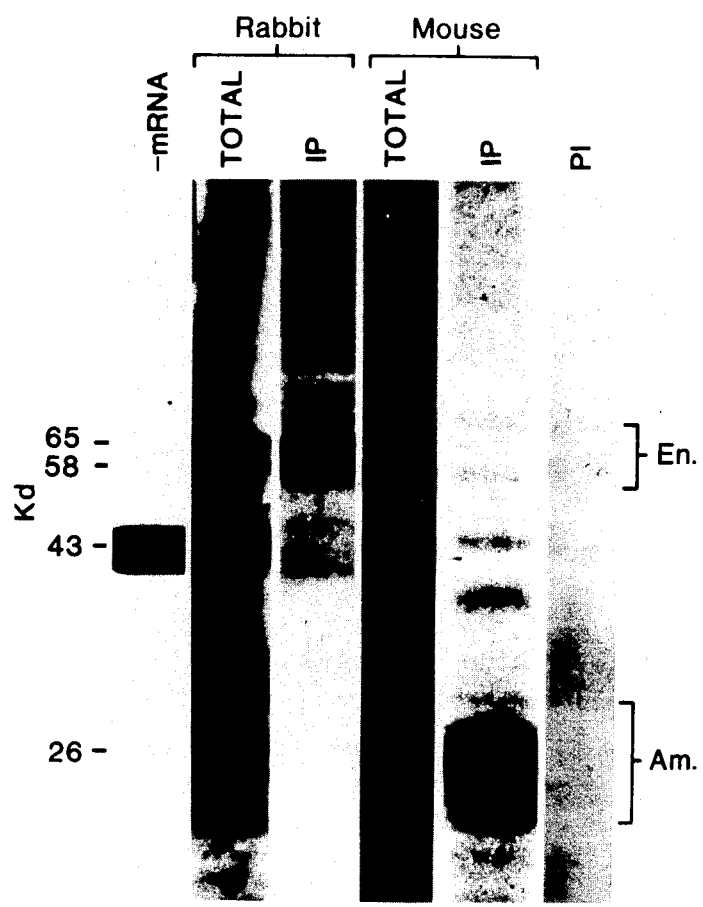
FIG. 5 shows the translation products of rabbit and mouse enamel organ epithelia total poly(A)containing RNA (IP indicates the immunoprecipitates with anti-enamelin or anti-amelogenin specific antibodies, PI indicates preimmune serum)

Postnatal mouse molar RNA's were isolated and the enamel mRNA's from murine were compared with rabbit-derived enamel mRNA's according to translational activity. Results of translation in the reticulocyte-lysate cell-free system showed considerable differences between mouse and rabbit enamel mRNA's. The major translation products using mouse enamel mRNA are four proteins of approximately 62, 28, 26 and 22 kd (not detected when testing rabbit molar mRNA translational activity). The mouse mRNA's have been partially characterized by specific immunoprecipitation of their respective translation products. The mouse poly(A)-containing RNA's contain an enamelin mRNA which codes for a 62 kd polypeptide, as well as three other amelogenin mRNA's which code for 28, 26 and 22 kd amelogenin polypeptides. All four enamel translation products are immuprecipitated with polyclonal antibodies directed against amelogenins. In contrast, mRNA's from rabbit ameloblasts appear to code for two enamelin polypeptides of 65 and 58 kd, as is shown in FIG. 5. Therefore, the mouse gene products can be cloned to obtain one enamelin and several amelogenin specific nucleotide sequences, whereas the rabbit gene products can be cloned to obtain several enamelin-specific nucleotide sequences. Evidence suggests that human enamel proteins are very similar in electrophoretic mobility, amino acid composition, and antigenicity to the enamelin present in rabbit and the three amelogenins present in the mouse.

Example IV

Production of Enamel Protein DNA Lineages

A. Isolation of Enamel Organ Epithelial Specific mRNA and Cloning of Its complementary DNA Poly-adenylated messenger RNA's (mRNA's) from enamel organ epithelium are isolated from fetal or neonatal teeth following the hereinbefore described procedure of Example Three. These RNA's contain all species of messenger responsible for the in vivo construction of the enamel matrix. Consequently, the cDNA synthesized to these RNA's represent the complete repetoire for enamel organ gene product(s). The production of a cDNA library is outlined below, and although the specific example of mouse is described, any vertebrate or primate enamel organ epithelial source may be employed.

The poly-adenylated mRNA's serve as templates for the enzymatic synthesis of complementary DNA (cDNA). The first strand of cDNA is synthesized by RNA-dependent DNA polymerase 480 U/ml [Avian myeloblastosis virus (AMV) reverse transcriptase] on oligo-d(T) (12 µg/ml) primed mRNA (20 µg/ml), in the presence of 40 µg/ml Actinomycin-D, deoxy-nucleotide triphosphates (dNTP each 1 mM) in 50 mM tris-HCl pH 8.3, 50 mM KCl, 10 mM $MgCl_2$, 40 mM $\beta$-mercaptoethanol, incubated at 46° C. for 30 minutes in a final volume of 250 µl.

The first strand of cDNA is isolated by centrifugation in alkaline 5–25 gm% sucrose gradient. This step serves to resolve synthesized cDNA by nature of their buoyant density as well as destroy the RNA template by alkaline hydrolysis, thus permitting size selection for full length cDNA's. The second strand cDNA is synthesized by self-priming in 50 mM tris-HCl pH 8.3, 10 mM $MgCl_2$, 42 mM $\beta$-mercaptoethanol, 1 mM each dNTP using 480 U/ml AMV reverse transcriptase in a final volume of 75 µl by incubation at 46° C. for 90 minutes.

The ds-cDNA is isolated by exclusion gel chromatography on acrylamide agarose composite matrix (Ac-A) and collected by centrifugation. The ds-cDNA is made blunt on either end by S-1 nuclease digestion, which insures that no single-stranded cDNA remains. The reaction conditions are 30 mM sodium acetate pH 4.5, 280 mM NaCl, 4.5 mM zinc acetate and 300 U S-1 nuclease, incubated at room temperature for sixty minutes. The nuclease is removed by buffered phenol extraction and the blunt-ended DNA recovered by AcA chromatography and ethanol precipitation.

The ds-cDNA is introduced to a vector moiety by utilizing homopolymer ends, synthetic linker oligonucleotides that contain a restriction endonuclease site, or by complementary restriction endonuclease digestion. In any case, oligonucleotides on the passenger (ds-cDNA) moiety are complementary to oligonucleotides on the vector moiety and by complementary base pairing re-anneal to one another. The method employed is d(C) homopolymer extension of the ds-cDNA and d(G) homopolymer extension of the restriction (Pst I) endonuclease digested (linearized) vector, pBR322. The reaction is simple and maintains the vector and passenger in a form that cannot re-anneal (circularize) to themselves. The tailing reaction is carried out in 200 mM potassium cacodylate pH 7.2, 1 mM cobalt chloride, 1 mM β-mercaptoethanol, 10 picomoles ds-cDNA termini, 5 U of deoxynucleotide terminal transferase, in a total volume of 400 μl at 37° C. until 15 residues have been added. A caveat is the difficulty of accurately determining the amount of termini to be extended. Therefore, test-tailing reactions are followed by radioactive incorporation to optimize the bulk-tailing reaction. In an identical procedure linearized vector is homopolymer tailed with a nucleotide complementary to the passenger homopolymer. When the vector pBR322 is linearized with the restriction endonuclease Pst I, and tailing is performed as outlined above, the restriction endonuclease recognition sequence can be reconstituted during the re-annealing procedure. We use the well characterized E. coli vector pBR322. This vector offers two antibiotic resistance sites, one of which can be inactivated when the passenger DNA is inserted. Therefore, recombinant transforming events are easily monitored by the conference of an ability to grow on nutrient plates containing the appropriate antibiotic. Moreover, the promoter sequence for the antibiotic resistance genes can be used for expression of the inserted passenger DNA. This property permits screening of recombinants by recognition of antigenic determinants on the synthesized protein programmed by the insertion of the passenger cDNA. Additionally, recovery of the foreign protein is achieved in analytical and preparative amounts by increasing the amount of transformed E. coli grown. Other methods for achieving the synthesis and processing of proteins coded by exogenous (foreign) DNA in a variety of host cells are discussed hereinafter.

The following protocol is used for annealing homopolymer d(C) tailed passenger DNA to Pst-I linearized homopolymer d(G) tailed vector (pBR322) DNA. Passenger and vector DNA are re-annealed in a molar 1:1 ratio in 10 mM tris-HCl pH 7.6, 100 mM EDTA in 400 μl volume. The mixture is heated to 68° C. for 30 minutes to minimize interfering secondary structure in the homopolymer tails, held at 42° C. for three hours, and allowed to cool overnight to room temperature.

The E. coli host, strain K-12 RR1 (a Rec A+ derivative of HB101), is prepared to be transformed by the recombinant DNA by treating exponential growth phase culture with ice cold 0.1M NaCl, 5 mM Tris-HCl pH 7.6 followed by an ice cold wash in 100 mM CaCl₂, 250 mM KCl, 5 mM Tris-HCl pH 7.6, 5 mM MgCl₂. The wash in CaCl₂ renders the host cell partially permeable to the recombinant DNA. The treated host cells are combined with the recombinant DNA in a volume ratio of 10:1, incubated for 60 minutes at 5° C., portions are spread onto nutrient agar plates containing the appropriate antibiotic, and permitted to grow. Growth indicates that the host has newly acquired resistance to the antibiotic conferred by the plasmid vector which is only infectious if successfully re-annealed with passenger DNA. Growth in the presence of antibiotic is the initial screening for productive recombinant DNA transformation. Transformation is similarly performed with either linearized homopolymer tailed pBR322 (negative control, noninfectious) or native pBR322 (positive control, infectious) to access the success of the transformation event compared to controls. A caveat of the reannealing protocol is to establish the optimal ratio of passenger DNA to vector DNA by trial. The optimal ratio is established by comparing the number of successful infections occurring at various volume ratios compared to positive and negative controls.

Initial screening of the transformed host is performed by the conference of the antibiotic resistant phenotype as outlined. Subsequent screening is performed at the nucleic acid level.

B. Identification and Isolation of Clones Containing Enamel Specific DNA Sequences by Nucleic Acid Hybridization A variety of strategies are available, selection being dependent on the exact circumstances of the cloning protocol. Nevertheless, all strategies take advantage of the physical fact that complementary nucleic acids will base-pair under proper conditions. Therefore, identification of host cell clones containing a segment of DNA of interest is made by permitting a radiolabeled or otherwise identified nucleic acid to hybridize to the immobilized DNA of the cloned host cells. A positive hybridization indicates that the host cell clone contains the inserted nucleic acid sequence of interest. Identification is performed by exposure of immobilized radiolabeled hybridized DNA to light sensitive films in the case of a radiolabelled nucleic acid probe.

The following protocols are utilized to delineate recombinant molecules of interest from the large number of transformants produced in the cloning procedure.

1. Colony Hybridization

Transformants are grown in an ordered array, in duplicate, on nutrient agar containing the antibiotic of choice. To facilitate immobilization of approximately equal amounts of DNA, the colonies are grown to the same extent, and transferred by mechanical means to a solid support consisting of nitrocellulose or cellulose filters. The DNA is fixed by heating at 68° C. and denatured by washes in 0.5N NaOH, 0.5M-Tris.HCl pH 7.4, and finally 0.3M NaCl, 0.03M sodium citrate (2×SSC). The DNA is then hybridized to a probe of interest. For example, this could be a radioactive single-stranded cDNA (synthesis outlined previously), made to the mRNA of interest. Hybridization solution consists of 6×ssc, 1 mM EDTA, 0.5 gm % sodium dodecyl sulfate (SDS) and 2×Denhardts (0.04 gm % each, bovine serum albumin, ficol, polyvinyl-pyrolidone) containing $10^6$ counts per minute of probe per milliliter solution at 68° C.

Figure 6:
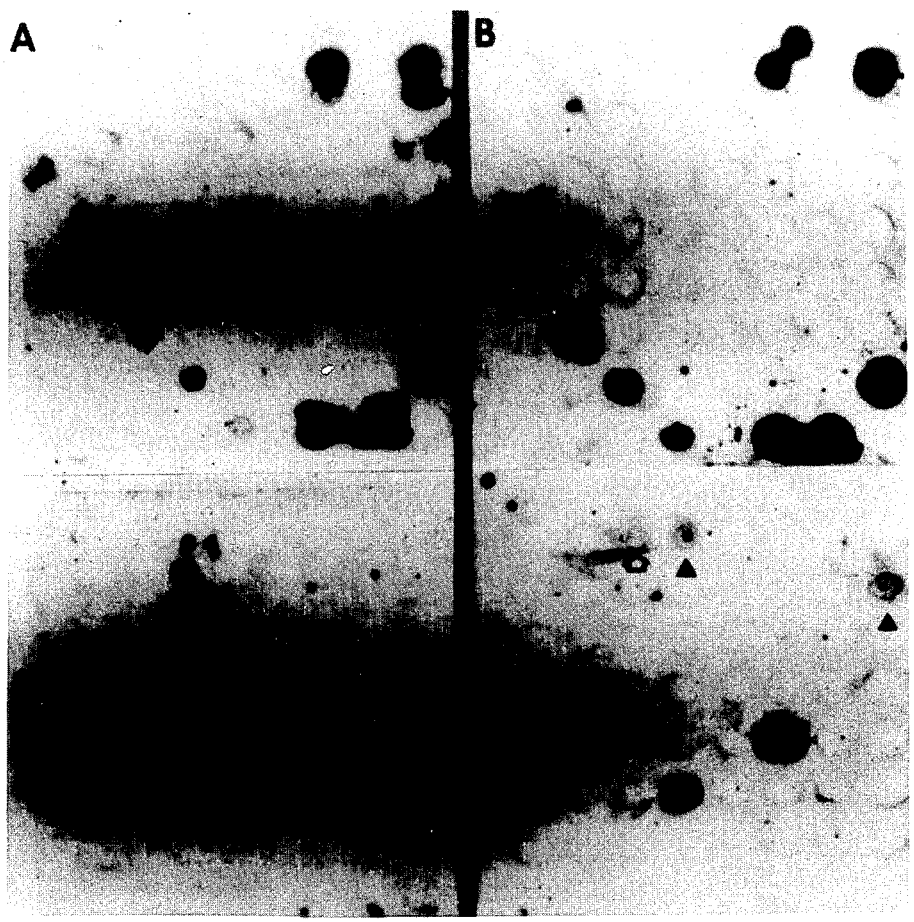
FIG. 6 depicts the colony hybridization of cDNA clones.

To eliminate false positive signals due to the cloning of "housekeeping" products, hybridization using radiolabeled cDNA probes to tissue-specific (enamel organ epithelium) versus non-tissue specific (liver) mRNA is performed on duplicate immobilized DNA. Stringent washing of the filters following hybridization in 2×SSC, 0.5 gm % at 68° C. reduces background and aids in recognition of an authentic enamel specific signals. An example of this assay is shown in FIG. 6, wherein the colonies were replica plated and bound to nitrocellulose filters, and the filters were hybridized to [$^{32}$P]-cDNA made to either (A) non-tissue specific or (B) tissue specific poly A+ mRNA. Enamel specific signals were detected in Panel B and not in Panel A.

2. Bi-directional Southern Blots

Cloned DNA is isolated in analytical quantities by the method of Birnboim and Doly [Birnboim, H. C., and Doly, S., *Nucleic Acid Res.* 7: 1513-1523 (1979)], linearized by restriction endonuclease digestion (BamHI) and resolved by 1% agarose gel electrophoresis. The DNA is transferred to duplicate nitrocellulose filters and hybridized to high specific activity cDNA made to tissue specific or non-tissue specific poly-A mRNA. Differential hybridization signals are interpreted as in above. Moreover, this method indicates the size of the inserted DNA aiding in the screening for full-length cDNA clones.

Figure 7:
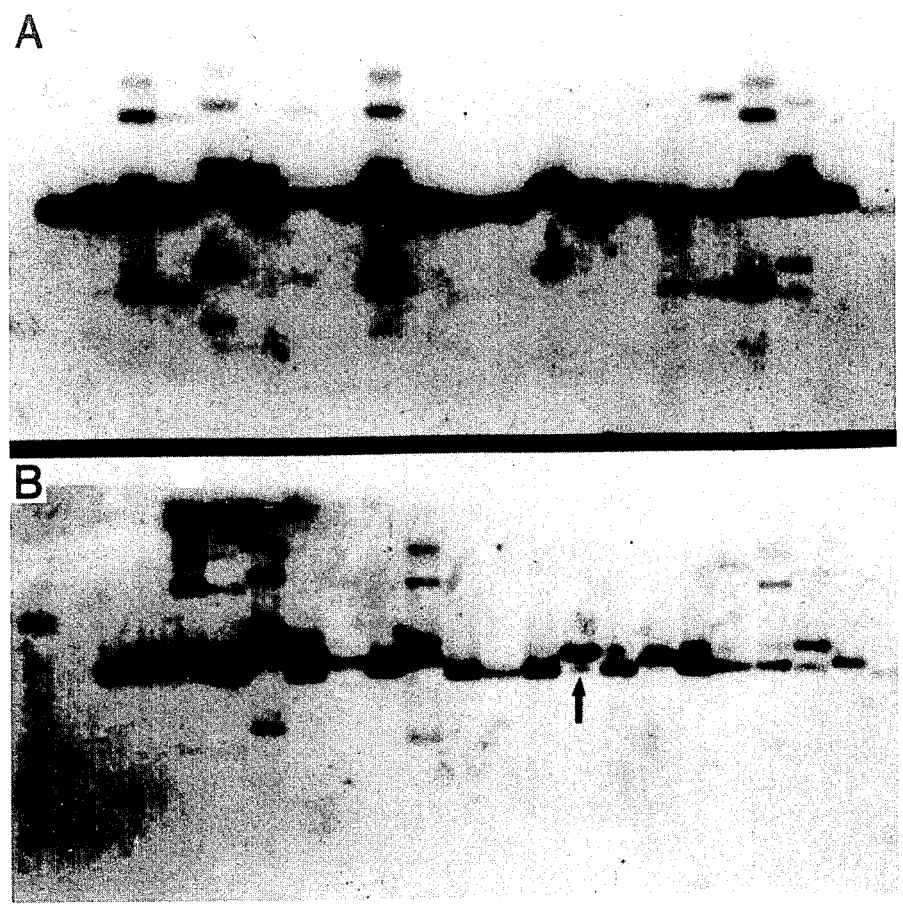
FIG. 7 shows differential hybridization to bidirectional Southern filters, wherein identical filters were hybridized to either high specific activity cDNA made to A) tissue specific (mouse organ epithelium), or B) non-tissue specific (liver) poly $A^+$-mRNA.

In a specific example, cloned DNA's which produced positive signals by colony hybridization, were isolated and linearized with restriction endonucleases, electrophoresed in 1% Agarose and transferred bi-directionally to nitrocellulose filters with 20×SSC. The filters were hybridized for 12 hours to $^{32}$P-cDNA's made to either tissue specific or non-tissue specific mRNA sources. Strong hybridization signals to tissue-specific cDNA probes compared to signals from non-tissue specific probes indicate clones which contain sequences for enamel specific products. An example of the result of this screening technique is shown in FIG. 7.

3. Hybrid Selected Translation and Immunoprecipitation

This method takes advantage of base-pair complementarity between messenger RNA and the coding strand of the recombinant DNA. DNA isolated from clones are immobilized on a solid support (nitrocellulose filters, derivitized cellulose etc.) and hybridized to total messenger RNA from the tissue source initially used. The DNA-RNA hybrid is thermally eluted and the selected RNA used to program a cell-free translation system. Immunoprecipitation of the translated product indicate whether the tested clone contains sequences complementary to the mRNA that codes for the protein of interest. A caveat is the possibility of a false positive signal generated by non-specific adherence of the mRNA (especially in high abundance systems) and its subsequent identification by immunoprecipitation of translated products. False signals can be reduced by diluting the mRNA of interest with a non-specific mRNA species thereby reducing the facility for non-specific adherence. Moreover, stringent washes of the DNA-RNA hybrid reduce the problem to background levels. A negative signal is generated by control (usually the vector alone) DNA similarly immobilized, being ineffective in selecting the messenger of interest. Fidelity of the hybridization is judged by accessing the mass of the selected product versus serial dilution of the pre-hybridization mRNA mixture after immunoprecipitation. This method has been published [Noyes, B. E., and Stark, G. R., *Cell* 5, 301 (1975); and Godburg et al., *Methods in Enzymology*, Ed. R. Wu 68: 206 (1979), and the latter method may be used without modifications.

Figure 8:
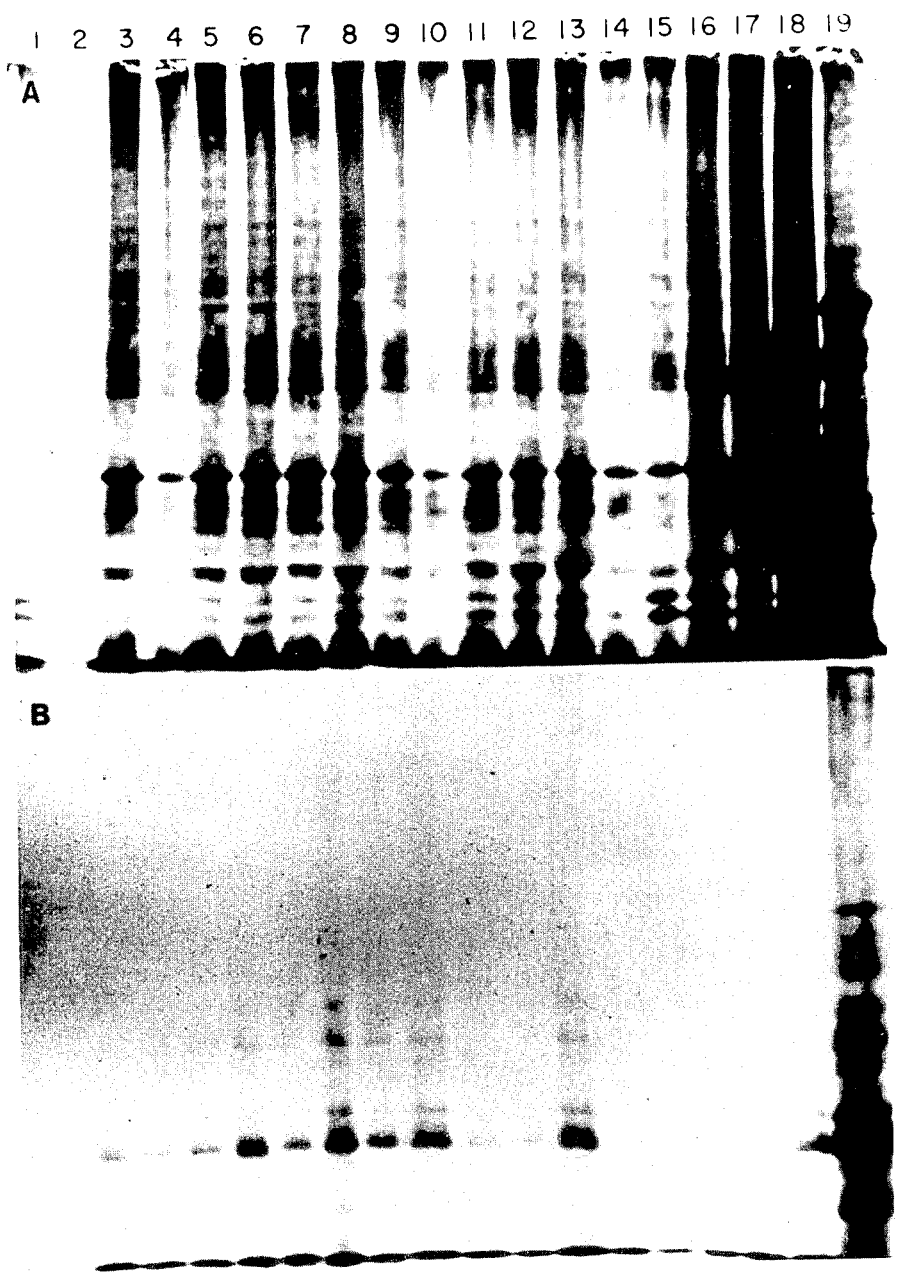
FIG. 8 is a fluorograph of translated mRNA hybrid-selected by recombinant clones.

In one example, candidate recombinant clones were further analyzed by hybrid-selected translation. Plasmid DNA's were isolated and digested with HhaI, were denatured and then coupled to benzyloxymethylcellulose. The immobilized DNA was allowed to hybridize with a mixture of mouse enamel organ and total mouse liver poly(A)-mRNA in a 1/20 ratio, respectively, in order to minimize false positive signals due to non-specific binding of the abundant mouse ameloblast mRNA. RNA's eluted from the columns were translated in vitro and total protein products were analyzed by NaDodSO$_4$/polyacrylamide gels and visualized by fluorography (FIG. 8, Panel A). The remaining translation products were immunoprecipitated with polyclonal antibody to mouse amelogenin and analyzed (FIG. 8, Panel B). Products synthesized in response to mRNA selected by the cloning vector pBR322 served as the negative control as shown in Lane 1, FIG. 8. The profile was similar to total liver poly(A)-mRNA. The major protein products synthesized in response to RNA and selected by candidate clones, appear to represent amelogeninspecific nucleotide sequences (FIG. 8, Panel A, Lane 13). These translated protein bands were immunoprecipitated with amelogenin antibody (FIG. 8, Panel B, Lane 13), which indicates that selected clones do contain mouse amelogenin sequences. The relative abundance of the selected message is demonstrated by comparison of translation protein band intensity to 1 μg hybridization mixture, serially diluted three-fold (FIG. 8, Lanes 15, 16, 17 and 18, respectively). Specifically with regard to FIG. 8, the total translation products are shown in (A). The immunoprecipitated products using rabbit anti-mouse amelogenin antibody are shown in (B). Lane 1 shows negative controls consisting of cloning vector pBR322; Lane 2 contains endogenous lysate products (no RNA added); Lanes 3–12 contain pooled mixtures of candidate cDNA clones for amelogenins; Lane 13 contains pMA 5/5; Lane 14 contains pMA 7/26; Lanes 15–18 contain three-fold serial dilutions of mRNA driver mixtures which contain 2 ng, 5 ng, 16 ng and 48 ng of enamel organ epithelia-specific mRNA, respectively; Lane 19 contains 1 μg of mRNA from two-day post-natal mouse molar tooth organs.

4. DNA Sequencing

Since partial N-terminus amino acid sequence data is available for several mammalian species of amelogenins, this technique is used for final authentication of recombinant molecules to enamel protein. For clones using pBR322 with homopolymer tails, we employ the method of Maxam and Gilbert [Maxam, A., and Gilbert, W., *Proc. Natl. Acad. Sci. USA* 94: 560–564 (1977)]: This is a base-specific chemical modification followed by base excision and strand separation of a sequence of DNA enjoying a radiolabeled nested end. Resolution of these fragments is by ultrathin poly-acrylamide gel electrophoresis from which the base sequence is read by exposure to light sensitive emulsion.

The Sanger method (di-deoxy termination) is used to sequence fragments where homopolymer tracks do not exist. These fragments are generated during sub-cloning of cDNA's or genomic DNA to a yeast, or selected eucaryotic host cell line [Sanger, F., Nicklen, S. and Coulson, A. R., *Proc. Natl. Acad. Sci. USA* 74:5463–5468 (1977)].

Figure 9:
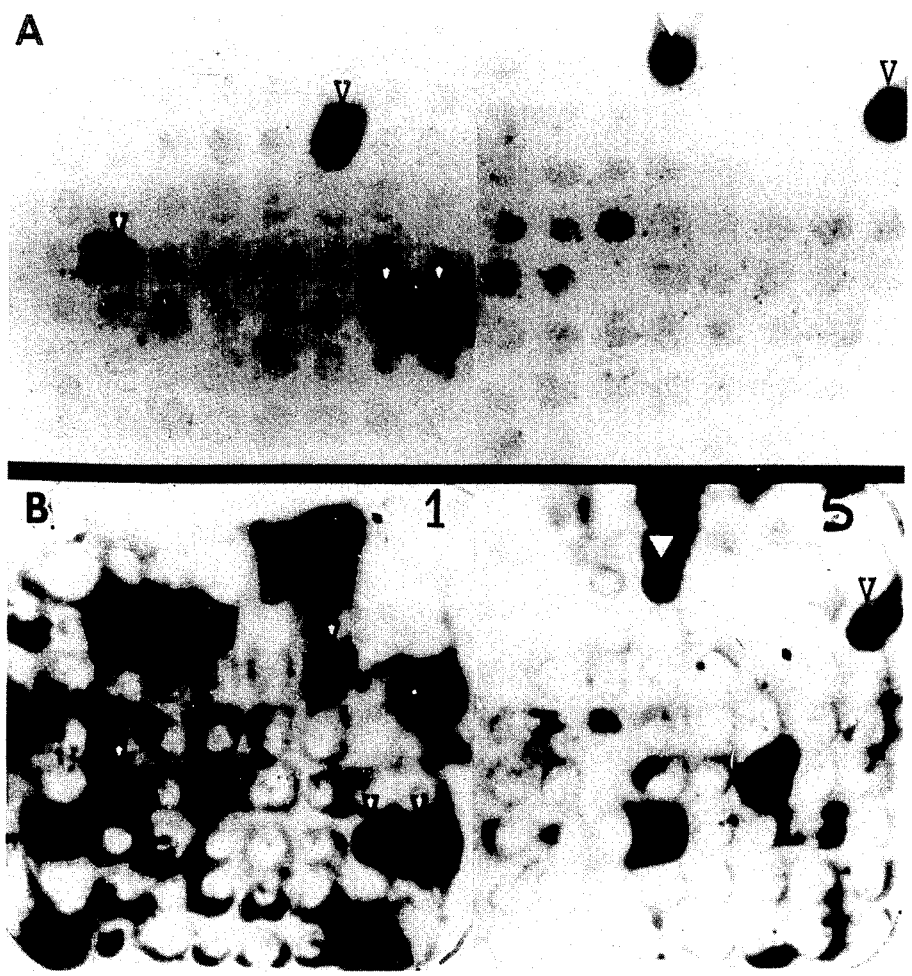
FIG. 9 shows colony identificaticn by backscreening, wherein the colonies from the cDNA library to mouse enamel organ epithelium were immobilized on nitrocellulose filters, hybridized to nick-repaired clone pMa 5—5 and identified by visualization on radiographic film.

In a specific example, a cDNA library to mouse enamel organ epithelium was produced by the methods previously described. This library thus contained all species of mRNA required for enamel formation in vivo, as complementary cDNA sequences. A clone designated pMa 5—5 was identified as an authentic amelogenin clone by the methods outlined in Example Four. The coding sequence for this amelogenin clone (pMa 5—5) was then used as a radiolabelled probe to identify from the library other amelogenin-containing sequences by colony hybridization. From a total of 570 transformants, 76 (13%) of the recombinants contained amelogenin sequences as determined by the radiograph set forth as FIG. 9. Another of these clones, designated pMa 2-12, was selected for Maxam and Gilbert sequence analysis. The results of this analysis are shown in Tables V and VI.

The known amino acid sequence data for amelogenins is shown in Table IV. It should be noted that there are significant conservation of amino acids in the phylogeny of enamel proteins amongst a wide variety of vertebrates. Table VII shows the theoretical N-terminal coding sequence for bovine amelogenin. Of this partial sequence, at least the first thirty-three amino acids and codons are thought to be the same for all mammalian amelogenin.

5. Characterization of Enamel Gene Clones by Restriction Endonuclease Digestion In addition to the methods of identification and characterization previously denoted, digestion of cloned DNA sequences by restriction endonucleases offers a powerful tool for identification of DNA sequences. Restriction endonucleases specifically recognize and introduce double-stranded cuts into unique stretches of DNA by nature of the DNA's primary nucleotide order. It is thus possible to characterize a segment of DNA by restriction endonuclease digestion. The fragments generated from such an analysis can be analyzed by separating them by polyacrylamide gel electrophoresis, agarose gel electrophoresis and other means. These fragments can be recovered from such analytical procedures and used as probes, subcloning into expression vectors, transferring into other host cell lines, or for nucleotide sequence analysis. In a specific example an authentic cDNA to murine amelogenin, pMa 5—5, was analyzed by restriction endonuclease digestion. The conditions of the reaction were those of the supplier of the restriction endonuclease enzyme. A map, based on restriction endonuclease nuclease sites for pMa 5—5 is presented as Table VIII. The 160 bp (base pair) DdeI fragment is characteristic of all the murine amelogenin cDNA characterized from the murine enamel organ epithelial library.

C. Identification of Enamel Genes From Gene Libraries

In addition to the cloning of specific enamelin or amelogenin cDNA's, it is advantageous to clone genomic DNA sequences for enamelin or amelogenin. In the procedures previously outlined for the production of cDNA clones for either enamelins or amelogenins, the cDNA clones reflect the structure of the mRNA and, therefore, do not contain intervening sequences. Using either single- or double-stranded enamelin or amelogenin cDNA's as probes, a human gene library is screened for the genomic DNA sequences which contain enamel structural genes when genomic DNA coding for enamel specific genes is required. Schematically, the procedure for construction of human gene libraries and the isolation of selected structural genes have been well defined. Human genomic DNA is isolated from a cell, tissue or organ source and then the high molecular weight DNA is digested with restriction endonucleases to produce random fragments of genomic DNA. These DNA genomic fragments are then joined to a vector such as bacteriophage λ, plasmids or cosmids. These vectors often have selectable markers which enable transformed bacteria or other cells containing recombinant DNA to be identified. Host cells containing gene sequences of interest are identified by nucleic acid hybridization as previously described, using cloned cDNA to the sequence of interest as a probe. The major advantage for identifying cloned genomic sequences for enamel structural genes is to use them as a source of DNA for transforming other suitable eucaryotic host cells which can then transcribe and/or translate the foreign exogenous DNA sequence. The utility of cloned cDNA for enamel proteins to screen a genomic library is shown below.

Figure 10:
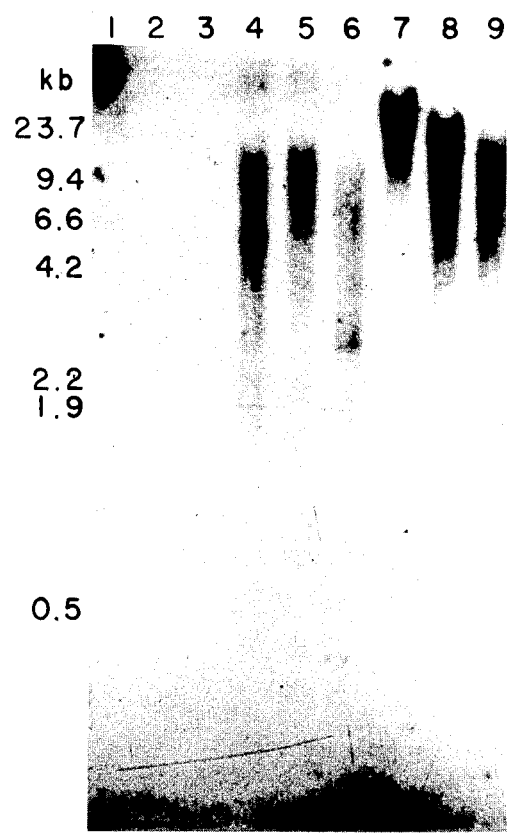
FIG. 10 is an autoradiogram of mouse and human genomic DNA sequences recognized by hybridization to nick-repaired clone pMa 5—5.

In a specific example, genomic high molecular DNA's were isolated and digested separately with restriction endonucleases. The resulting fragments were separated in 1% agarose by electrophoresis, and transferred to nitrocellulose filters using the method of Southern (Southern, E. M. (1975) *J. Mol. Biol.* 98, pp. 503–517). The filter was hybridized for twelve hours to Pst I excised [$^{32}$p]-nick-repaired probe pMa 5—5, specific activity=$1-2 \times 10^8$ cpm/µg and washed under stringent conditions of salt and temperature (Maniatis, T., Jeffrey, A. and Kleid, D. G. (1975) *Proc. Natl. Acad. Sci. USA* 72, pp. 1184–1188.) The autoradiogram shown in FIG. 10 was exposed for thirty-six hours to detect hybridization of the radiolabelled probe to specific genomic DNA sequences flanked by restriction endonuclease sites. Lane 1 contains Lambda-phage DNA digested with Hind III from which the sizes in kilobase pairs (Kb) were determined and are shown to the left. Lanes 2 and 3 each contain 10 µg *E. coli* DNA digested with Eco RI, Bam HI and Hind III, respectively. Lanes 4, 5, 6 each contain 10 µg of mouse DNA digested with Eco RI, Bam HI and Hind III, respectively. Lanes 7, 8, 9 each contain 10 µg of human DNA digested with Eco RI, Bam Hi and Hind III, respectively. The presence of amelogenin sequences is proven by the observation of hybridization signal from both mouse and human genomic DNA's. Thus, the murine amelogenin cDNA clone pMa 5—5 serves as a useful probe for the identification of amelogenin sequences from a human genomic library. Moreover, the probe pMa 5—5 could equally serve as a probe for the identification of amelogenin sequences from other lower vertebrate or primate genomic DNA libraries.

Example V

Production of Transformed Cells Which Express Enamel Gene Products

A. Expression in Bacteria

Expression vectors contain sequences of DNA that are required for the efficient transcription of foreign cloned genes and the translation of the resulting messenger RNA (mRNA) in the host. This requires three steps: (i) placing the foreign gene sequence under the control of a host cell promoter which is efficiently recognized by the host cells RNA polymerase (i.e. transcription); (ii) insuring that the generated mRNA is relatively stable; and (iii) ensuring that the mRNA is efficiently translated to a complete protein. The foreign protein must be recoverable and should not be rapidly degraded by host cell proteases. There are two basic approaches to the expression of mammalian enamel protein gene sequences in bacteria. First, the cloned mammalian sequence is spliced to a bacterial gene promoter sequence so that the bacterial initiation codon is followed directly by the codon for the first amino acid of the mammalian protein. This produces a mammalian protein unfused to a bacterial protein, which is under the control of an *E. coli* promoter, and maintains the Shine-Delgarno sequence required for optimal translation occurring by recognition of the mRNA transcript by E. coli 16S ribosomal RNA [Shine, J., and Delgarno, L., Nature 254:34-37 (1925)].

The second method involves inserting mammalian coding sequence into an internal position to a bacterial gene so that the insert is in phase with the bacterial coding sequence. This process results in the synthesis of a hybrid bacterial-mammalian protein. A disadvantage is that the protein of interest must be released from the hybrid molecule, however, this has been achieved. The advantages to this approach are (i) minimal chance of disturbing the mRNA secondary structure in the area of the ribosome binding site and initiation codon causing a reduced rate of protein synthesis, (ii) reduced degradation of foreign proteins when fused to a bacterial protein thereby increasing the yield of the mammalian protein, and (iii) ease of construction of vectors for the synthesis of a hybrid molecule. This procedure is simpler than that for unfused synthesis since the latter method requires an ATG codon which, if not present in the foreign sequence, must be provided for by chemical DNA synthesis. A successful approach to efficient production of hybrid molecules has been published [Shine et al. Nature 285:456-561 (1980) and Goeddel, P.N.A.S. 76:106-110 (1979)]. The method utilizes the lac promoter to control the expression of the fused protein. The product of the lac Z gene sequence is an inducible, enzymatically active protein, β-galactosidase. This method, therefore, provides an enzymatic assay for the production of a foreign protein that does not otherwise have an assayable activity.

B. Expression in Yeast

The production of yeast clones follows a similar protocol using the appropriate vectors and yeast strains. Cloning in yeast cells has been less widely used due to restrictions from NIH recombinant DNA guidelines. Since 1980 these restrictions have been lifted, and attempts have been made to insert genes for globin, ovalbumin, herpes simplex virus thymidine kinase, etc., although not all of them successful. Nevertheless, yeast clones have the advantage of being able to carry out the post-translational modifications (e.g., acetylation, glycosylation, phosphorylation), characteristic of eucaryotic cells. These post-translational steps may be particularly advantageous in enamel protein biosynthesis.

A useful method to promote transcript of a foreign gene and subsequent translation into protein is by the construction of hybrid genes in which the eucaryotic sequence is fused, in phase, to a bacterial gene. Such an approach utilizes the E. coli lac Z gene coding for β-galactosidase and fuses it to the DNA in question, inserted into a plasmid and cloned in E. coli.

A similar approach is used to clone the specific enamel mRNA's in yeast. There is a small DNA fragment carrying the L8YV5 lac operator promoter region with information for the first eight amino acids of β-galactosidase, which has been engineered into a phage (c°1857 p°lac°L8UV5 Z having a unique Eco RI site located after the eighth amino acid of β-galactosidase). When this DNA is digested with Eco RI and Hind III, a fragment of 2.85 kilobases is generated which carries the beginning of the lac sequence. Five hundred nanograms of this phage DNA, and 50 µg of pBR322 DNA are digested with Eco RI and Hind III and ligated with T4 DNA ligase, resulting in a recombinant plasmid of approximately 7.1 Kb. This new plasmid is used to transform CaCl$_2$-treated E. coli strain 478 (C600 $r_k$°$m_k$°rec°BC− lac y). The transformants are selected on tryptone plates containing ampicillin (20 µg/ml) and 5-bromo-4-chloro-indolylgalactoside [X-gal], 40 µg/ml). Strains carrying the recombinant plasmid are resistant to ampicillin and are lac constitutive, thus producing blue colonies when grown on nutrient plates containing X-gal.

Thereafter, the cloned cDNA or genomic sequence containing the complete sequence for the enamel proteins is fused, in phase, to the beginning of the lac Z gene. The plasmid DNA (containing the lac sequence) is linearized with Eco RI. Both DNA's are treated with S1 nuclease to eliminate single stranded ends and blunt-end ligation is done with T4 DNA ligase. The cloned enamel DNA is pre-treated with the appropriate restriction enzyme in order to fuse with the β-galactosididase in the proper phase at an early sequence without losing the N-terminal sequence of the enamel protein. The recombinant molecules are introduced into E. coli, screened as previously described, and then tested for enamel protein expression with the use of a specific enamel antibody.

Transformation of yeast is done by recombining the lac-enamel DNA with vector pFLI (composite of pBR322 carrying part of the yeast 2 µm plasmid and the yeast selective marker ura3) which can be propagated in both E. coli or yeast. The pFLI DNA (∼30 µg) is digested with an appropriate restriction endonuclease that produces a fragment containing the full sequence of the lac-enamel gene. The linear plasmid molecules are purified by centrifugation on a 5-20% sucrose gradient (0.01M tris, pH 8.0; 0.01M EDTA and 0.1M NaCl) for four hours at 40,000 rpm at 20° in a Beckman SW-41 rotor. The linear pFLI DNA (600 µg) is ligated to 200 µg of the purified lac-enamel DNA, and the recombinant plasmids are amplified in E. coli. Ampicillin resistant clones are selected. The site of insertion of the lac-enamel DNA is determined by restriction mapping (digestions are carried out as recommended by the enzyme vendors). The selected recombinant plasmids are used to transform Saccharomyces cerevisiae strain ura3-251-373-326. Yeast is grown in yeast nitrogen base (Difco) containing 2% glucose at 29° C. Analysis of the structure of the yeast plasmid is done by resuspending transformed cells (picked from selective plates) in 300 µl of 0.005M tris-HCl, pH 8.0; 0.001M EDTA; 0.1% triton X-100, shaking vigorously at 4° C. with glass beads. The DNA is extracted with phenol and analyzed by restriction mapping. Analysis of yeast clones expressing enamel protein synthesis is performed as outlined.

C. Transformation and Expression in Eucaryotic Cells

The DNA or genomic clones isolated as described and shown to be encoding for enamel gene products are used to transform selected eucaryotic cell lines. In this manner specific genes are stably introduced into cultured mammalian cells by DNA-mediated transfer. Cloned DNA is mixed with salmon sperm DNA to a final concentration of 20 µg/ml in HEPES. buffered saline (8.0 g/l NaCl, 0.37 g/l KCl, 0.125 g/l Na$_2$HPO$_4$, 1.0 g/l dextrose and 5.0 g/l HEPES. pH 7.10), and made 125 mM to CaCl$_2$. The recipient mammalian cell line is grown for 3-5 doublings (∼10$^6$ cell/100 mm petri dish), the growth media aspirated and the cells overlaid with 0.5 ml of the previously prepared DNA/calcium phosphate mixture for 30 minutes. Growth media is applied for 24 hours, and transformed cells chosen in selection media. The Vero cell line is used, as these are deficient in thymidine kinase (Tk−) and obtainable from the American Type Culture Collection. Co-transfection is accomplished with either viral-Tk sequences or use of a chimeric plasmid composed of pBR322 and the Bam HI fragment of herpes simplex virus Tk to permit identification of an identifiable phenotype. Cells that have acquired the Tk+ genotype by DNA uptake are then selected for Tk+ phenotype by growth in selection media. The selection media contains HAT (hypozantine, aminopterin and thymidine) in which cell survival depends upon the presence of both purine salvage pathway enzymes, thymidine kinase and hypozantine guanosine phosphoribosyl transferase. Cell colonies resistant to HAT medium are screened for enamel sequences by nucleic acid hybridization and immunologic detection of synthesized enamel protein(s).

Another mammalian cell vector is the papova virus SV-40 from which the DNA coding, for the major capsid protein, VPI is removed by restriction endonuclease treatment and substituted with a cloned DNA segment of interest. This approach has been used to transform monkey kidney cells with modified SV-40 containing rabbit β-globin coding sequence. The transformed cells transcribed and translated the β-globin sequence in substantial amounts (Mulligan, et al. *Nature* 277:108–114 (1979)). These transformed cells can then be utilized as sources of transcription or translation products. Alternatively, inserted genomic DNA sequences are efficiently transcribed by higher eucaryotic cell lines and these resulting mRNA's used as templates for the synthesis of single or double stranded cDNA.

D. Identification By Immunologic Determinants

Since antibodies to the desired protein product are available, a high level of confidence is conferred by identifying recombinants by immunologic criteria. We use assays which take advantage of cross reactivity between murine and human enamel proteins. Specific and general examples of these assays are as follows:

1. Preparation Of Agar Or Agarose Plates Containing the Specific Antibodies

The clones are transferred to the plates, incubated at 37° C. for 16 hours and the clones producing enamel gene products are detected by the immunoprecipitate (turbidity zone) surrounding the colony (*Methods in Enzymology*, 68:428 (1979)).

2. $^{125}$I-Labeled Antibody Assays

This assay may be employed when increased sensitivity is desired. The cold antibody is attached covalently to CNBr-activated paper which serves to immobilize the antigen. The paper is placed on top of the agar plates where the colonies potentially containing the enamel protein have been previously lysed. After incubation, the paper is removed, washed and incubated with $^{125}$I-labeled enamel protein antibody followed by autoradiography. This step serves to identify production colonies. Picograms of enamel protein synthesized by the clones can be detected. Since the antibody detects the presence of antigenic determinants in a molecule, even if it is not completed, it is necessary to ascertain by other means that the proteins synthesized by the clones are full-length polypeptide molecules. The physical and chemical properties of the artificially produced enamel proteins are determined and compared with native enamel proteins.

3. Immunoassay of Cell Protein Extract

The host cells containing the recombinant DNA molecule are grown overnight on nutrient agar plates containing the appropriate antibiotic. The colonies are lysed with an overlay of soft agar containing 10 mg/ml lysozyme and then transferred to nitrocellulose filters. Serial dilutions of the protein of interest are spotted onto another nitrocellulose filter and serve as positive controls for detection of minimal protein concentration. The filters are air dried and then washed in phosphate buffered saline (PBS) containing 0.5 gm % bovine serum albumin to minimize non-specific adherence of antibody. The filters are then exposed to 250 μg/ml of the IgG fraction of the rabbit anti-mouse amelogenin in PBS. The recognition of enamel protein determinants by the antibody are made detectable by exposing the filters to $^{125}$I labeled Staphylococcus Aureus Protein A (commercially available). Protein A has the ability to recognize and attach to the carboxy terminii of immunoglobins. Visualization of clones producing the protein of interest is made by exposing the filters to light sensitive emulsion.

A caveat is that 1 in 6 DNA insertional events occur in the proper reading frame for protein production. Therefore, comparison of data gained by immunologic criteria must be compared to nucleic acid hybridization data. However, this analysis does permit rapid detection of clones expressing the protein encoded by the foreign DNA and these clone(s) can be used for analytical and preparative purposes.

Thus it is seen that the isolation of human messenger RNA for enamel protein and cDNA cloning is performed using a pBR322 vector and *E. coli* as described. Positive transformants are then identified by colony hybridization and hybrid selected immunoprecipitation assay. Sequence information and other physical data are used to determine the clones which contain full length cDNA inserts for the enamel proteins. These sequences are inserted into expression competent vectors and appropriate hosts to optimize the synthesis of human enamel protein. Using the high transformation efficiency of pBR322 serves as an approach to produce a human enamel organ library from which desirable DNA segments may be drawn. These sequences are then subcloned into expression vectors from *E. coli*, yeast or mammalian cells.

From the foregoing description, one skilled in the art can readily ascertain the essential characteristics of the invention and, without departing from the spirit and scope thereof, can adapt the invention to various usages and conditions. Changes in form and the substitution of equivalents are contemplated as circumstances may suggest or render expedient; and although specific terms have been employed herein, they are intended in a descriptive sense and not for purposes of limitation, the purview of the invention being delineated in the following claims.

TABLE I

Amino Acid Composition of Enameloid or Enamel Matrix Proteins From Selected Vertebrate Species

| Amino Acid | Hagfish | Shark | Alligator | Rabbit | Mouse | Hamster | Sheep | Cow | Pig | Monkey | Human |
|---|---|---|---|---|---|---|---|---|---|---|---|
| Aspartic Acid | 89 | 148 | 55 | 85 | 93 | 52 | 58 | 38 | 28 | 28 | 34 |
| Threonine | 53 | 44 | 35 | 43 | 48 | 39 | 34 | 32 | 32 | 42 | 31 |
| Serine | 105 | 197 | 67 | 75 | 150 | 67 | 74 | 40 | 48 | 50 | 55 |
| Glutamic Acid | 100 | 161 | 153 | 122 | 137 | 160 | 175 | 202 | 196 | 156 | 161 |
| Proline | 8 | 56 | 208 | 72 | 135 | 159 | 262 | 248 | 242 | 264 | 247 |
| Glycine | 110 | 174 | 78 | 127 | 84 | 77 | 70 | 50 | 51 | 55 | 66 |
| Alanine | 64 | 54 | 32 | 79 | 62 | 60 | 51 | 32 | 26 | 21 | 15 |
| Valine | 53 | 23 | 34 | 36 | 53 | 45 | 50 | 38 | 37 | 42 | 36 |
| Methionine | 23 | 4 | 13 | 15 | 30 | 35 | 30 | 41 | 46 | 51 | 37 |
| Isoleucine | 47 | 19 | 34 | 40 | 32 | 35 | 37 | 33 | 37 | 25 | 32 |
| Leucine | 98 | 33 | 77 | 61 | 81 | 85 | 100 | 92 | 94 | 92 | 92 |
| Tyrosine | 30 | 11 | 55 | 17 | 22 | 31 | 27 | 26 | 32 | 52 | 71 |
| Phenylalanine | 20 | 9 | 31 | 26 | 24 | 26 | 26 | 26 | 23 | 16 | 22 |
| Histidine | 14 | 32 | 41 | 15 | 35 | 58 | 33 | 16 | 11 | 66 | 59 |
| Lysine | 122 | 21 | 61 | 52 | 27 | 40 | 48 | 63 | 87 | 17 | 19 |
| Arginine | 62 | 19 | 27 | 27 | 13 | 27 | 25 | 18 | 10 | 16 | 23 |

Results are expressed as residues/1000.

TABLE II

Amino Acid Composition of Selected Mammalian Enamelins and Amelogenins.

| | Enamelis[a] | | | Amelogenins[a] | |
|---|---|---|---|---|---|
| Amino acid | Rabbit | Bovine[b] | Hamster[c] | Bovine[b] | Hamster[c] |
| Aspartic acid | 84 | 98 | 80 | 38 | 30 |
| Threonine | 41 | 55 | 47 | 29 | 35 |
| Serine | 108 | 81 | 128 | 46 | 76 |
| Glutamic acid | 118 | 146 | 135 | 176 | 157 |
| Proline | 35 | 139 | 54 | 231 | 230 |
| Glycine | 188 | 114 | 138 | 56 | 55 |
| Alanine | 75 | 50 | 75 | 29 | 41 |
| Valine | 36 | 39 | 23 | 46 | 39 |
| Methionine | 18 | 23 | 51 | 51 | 25 |
| Isoleucine | 38 | 35 | 40 | 34 | 38 |
| Leucine | 60 | 94 | 55 | 103 | 100 |
| Tyrosine | 20 | 18 | 33 | 33 | 37 |
| Phenylalanine | 23 | 40 | 31 | 26 | 22 |
| Histidine | 19 | 12 | 40 | 68 | 73 |
| Lysine | 66 | 58 | 30 | 14 | 25 |
| Arginine | 29 | 18 | 11 | 19 | 18 |

[a]Residues/1000
[b]Taken from Termine et al. J. Biol. Chem. (1980) 255:9760-9768.
[c]Taken from Lyaruu et al. Calcif. tissue Int. (1982) 34:86-96.

TABLE III

Comparison Between Murine and Bovine Amelogenins Amino Acid Compositions

| | Murine Amelogenins[a] | | | | Bovine Amelogenins[b] | | | |
|---|---|---|---|---|---|---|---|---|
| Amino Acid | 1 | 2 | 3 | 4 | "B" | "F" | "FG" | "A" |
| Aspartic Acid | 56 | 50 | 36 | 48 | 28 | 51 | 49 | 38 |
| Treonine | 42 | 42 | 37 | 39 | 24 | 28 | 29 | 29 |
| Serine | 116 | 112 | 95 | 106 | 28 | 53 | 67 | 46 |
| Glutamic Acid | 151 | 149 | 162 | 151 | 219 | 107 | 112 | 176 |
| Proline | 201 | 197 | 241 | 216 | 277 | 239 | 220 | 231 |
| Glycine | 67 | 67 | 51 | 62 | 32 | 63 | 88 | 56 |
| Alanine | 51 | 51 | 44 | 49 | 26 | 21 | 0 | 29 |
| Cystine | ND | ND | ND | ND | ND | ND | ND | 1 |
| Valine | 42 | 43 | 40 | 42 | 39 | 25 | 32 | 46 |
| Methionine | 41 | 40 | 42 | 41 | 50 | 38 | 41 | 51 |
| Isoleucine | 34 | 32 | 35 | 33 | 37 | 32 | 34 | 34 |
| Leucine | 82 | 80 | 91 | 86 | 101 | 129 | 84 | 103 |
| Tyrosine | 25 | 42 | 30 | 29 | 26 | 53 | 85 | 33 |
| Phenylalanine | 18 | 20 | 18 | 20 | 17 | 37 | 34 | 26 |
| Histidine | 50 | 47 | 63 | 52 | 82 | 55 | 64 | 68 |
| Lysine | 23 | 13 | 13 | 16 | 7 | 34 | 31 | 14 |
| Arginine | Traces | 13 | Traces | 13 | 7 | 32 | 29 | 19 |

Results are expressed as Residues/1000.
[a]The mouse amelogenin family of proteins were divided into three sub-classes with molecular weights of approximately 28,000 (1), 26,000 (2) and 22,000 (3). The average composition is indicated in column 4.
[b]The composition data of bovine amelogenins was taken from Bio-Gel P30 regions: "B" (27-30,000 mol. wt.); "F" (10,000 mol. wt.); "FG" (lower than 10,000) from Fincham et al. Calcif. Tissue Int. 34:182-189 (1982) and "A" from Termine et al. J. Biol. Chem. 255:9760-9768 (1980).

TABLE IV

Amino Acid Sequence of the Amino Terminal Region of Porcine, Bovine, Human and Murine Amelogenins

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Porcine 2a[1] | MET | PRO | LEU | PRO | PRO | HIS | PRO | GLY | HIS | PRO | GLY | TYR | ILE | ASP | PHE | SER | TYP | GLU |
| Porcine 2b[1] | MET | PRO | LEU | PRO | PRO | HIS | PRO | GLY | HIS | PRO | GLY | TYR | ILE | ASP | PHE | SER | TYP | GLU |
| Bovine | MET | PRO | LEU | PRO | PRO | HIS | PRO | GLY | HIS | PRO | GLY | TYR | ILE | ASP | PHE | SER | TYP | GLU |

TABLE IV-continued

Amino Acid Sequence of the Amino Terminal Region of
Porcine, Bovine, Human and Murine Amelogenins

| | |
|---|---|
| Bovine TRAP[2] | MET—PRO—LEU—PRO—PRO—HIS—PRO—GLY—HIS—PRO—GLY—TYR—ILE—ASP—PHE—SER—TYP—GLU |
| Bovine LRAP[2] | MET—PRO—LEU—PRO—PRO—HIS—PRO—GLY—HIS—PRO—GLY—TYR—ILE—ASP—PHE—SER—TYP—GLU |
| Human[3] | MET—PRO—LEU—PRO—PRO—HIS—PRO—GLY—HIS—PRO—GLY—TYR—ILE—ASP—PHE—SER—TYP—GLU |
| Mouse | MET—PRO—LEU—PRO—PRO—HIS—PRO—GLY—HIS—PRO—GLY—TYR—ILE—ASP—PHE—SER—TYP—GLU |

| | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| Porcine 2a[1] | VAL—LEU—THR—PRO—LEU—LYS— X —TYR—GLU—SER—MET—ILE— X —HIS—PRO—TYR—THR—SER |
| Porcine 2B[1] | VAL—LEU—THR—PRO—LEU— X — X —TYR—GLU—SER—MET—ILE— X —HIS—PRO—TYR—THR—SER |
| Bovine TRAP[2] | VAL—LEU—THR—PRO—LEU—LYS—TRP—TYR—GLN—SER—MET—ILE—ARG—HIS—PRO—TYR—SER—PRO |
| Bovine LRAP[2] | VAL—LEU—THR—PRO—LEU—LYS—TRP—TYR—GLN—SER—MET—ILE—ARG—HIS—PRO—PRO—LEU—PRO |
| Human[3] | VAL—LEU—THR—PRO—LEU—LYS—TRP—TYR—GLN—SER—ILE —MET |
| Mouse | VAL—LEU—THR—PRO—LEU—LYS—TRP—TYR—GLN—SER—MET—ILE |

| | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| Porcine 2a[1] | TYR—GLY—THR—GLU—PRO—MET—GLY—GLY— X —LEU—HIS—HIS—GLU—ILE—ILE—PRO—VAL—VAL |
| Porcine 2b[1] | TYR—GLY—THR—GLU—PRO—MET—GLY—GLY— X —LEU—HIS—HIS—GLU—ILE—ILE—PRO—VAL—VAL |
| Bovine TRAP[2] | TYR—GLY—TYR—GLU—PRO—MET—GLY—GLY—RP |
| Bovine LRAP[2] | PRO—MET—LEU—PRO—ASP—LEU —PRO—LEU—GLU—ALA |

[1]From Fukae et al. Tsurumi Univ. Dent.J., 6:87-94 (1980) Fragments 2a and 2b are peptides obtained by cleavage with clostridiopeptidase B of amelogenins 26 kd and 21 kd respectively from porcine immature enamel.
[2]Fincham et al. Biosci. Rep., 1:771-778 (1981) Fetal Bovine amelogenins rich in tyrosine (TRAPO or leucine (LRAP)
[3]From Fincham et al. Biochem. J. (1983) (In Press)

TABLE V

| HpaII—HinFI Fragment |
|---|
| CCTTGGTCTG ACACCACCAG CAGTTTCAAT CAAGAAAGAG CTCTCAA. |

TABLE VI

| HinFI—HpaII Fragment |
|---|
| CCATTGCTTA CTCTTGAAGA ACGAACACCA TTTCTGTAAG CTGGTGAC. |

TABLE VII

Partial mRNA Sequence Which Codes For The
N-Terminal Sequence Of Bovine
Amelogenin Polypeptides

| 1 | 2 | 3 | 4 | 5 | 6 | 7 | 8 | 9 | 10 | 11 | 12 |
|---|---|---|---|---|---|---|---|---|---|---|---|
| MET | PRO | LEU | PRO | PRO | HIS | PRO | GLY | HIS | PRO | GLY | TYR |
|  | U | U | U | U |  | U | U |  | U | U |  |
|  | C | C | C | C | U | C | C | U | C | C | U |
|  | A | A | A | A | A | A | A | C | A | A | C |
|  | G | G | G | G |  | G | G |  | G | G |  |

| 13 | 14 | 15 | 16 | 17 | 18 | 19 | 20 | 21 | 22 | 23 | 24 |
|---|---|---|---|---|---|---|---|---|---|---|---|
| ILE | ASN | PHE | SER | TYR | GLU | VAL | LEU | THR | PRO | LEU | LYS |
| U |  | U | U |  |  | U | U | U | U | U |  |
| C | U | C | C | U | A | C | C | C | C | C | A |
| A | C | | A | C | G | A | A | A | A | A | G |
|  |  |  | G | | | G | G | G | G | G | |

| 25 | 26 | 27 | 28 | 29 | 30 | 31 | 32 | 33 | 34 | 35 | 36 |
|---|---|---|---|---|---|---|---|---|---|---|---|
| TRP | TYR | GLU | SER | MET | ILE | ARG | HIS | PRO | TYR | THR | SER |
|  |  |  | U |  |  | U |  | U |  | U | U |
|  | U | G | C |  | U | C | U | C | U | C | C |
|  | C | A | A |  | C | A | C | A | C | A | A |
|  |  |  | G |  |  | G |  | G |  | G | G |

| 37 | 38 | 39 | 40 | 41 | 42 | 43 | 44 | 45 | 46 | 47 | 48 |
|---|---|---|---|---|---|---|---|---|---|---|---|
| TRY | GLY | THR | GLU | PRO | MET | GLY | GLY | TRP | LEU | HIS | HIS |
|  | U | U |  | U |  | U | U |  | U |  |  |
| U | C | C | A | C |  | C | C |  | C | U | U |
| C | A | A | G | A |  | A | A |  | A | C | C |
|  | G | G |  | G |  | G | G |  | G |  |  |

Genetic code from: Biochemical Genetics, R. A. Woods, Chapman and Hall. London and New York 1980

TABLE VIII

Restriction Endonuclease Cleavage Map For pMa 5-5

```
BglI——||—PstI—HinFI—HinFI—DdeI—DdeI—PstI——||—EcoRI
         90bp  140bp  180bp  160bp  80bp
```

What is claimed is:

1. A method for the formation of dental enamel crystals comprising mixing a solution containing calcium ions and phosphate ions with a mixture of proteins including an enamelin having a weight of from about 62 to 72 kd and an amelogenin having a weight of about 26, 28.5 or 30 kd in an enamelin-amelogenin ratio of about 1:10, in the presence of a catalytically effective amount of a serine protease at a pH of from about 7.2 to about 8.1 and at a temperature which retains the catalytic activity of the serine protease and results in the formation of dental enamel crystals.

2. The method of claim 1 wherein said solution is supersaturated with calcium phosphate.

3. The method of claim 1 or 2 wherein the solution further includes at least 5 ppm fluoride.

4. A method for the formation of dental enamel crystals comprising mixing a solution containing calcium ions and phosphate ions with a mixture of proteins including an enamelin having a weight of from about 62 to 72 kd and an amelogenin having a weight of about 26, 28.5 or 30 kd in an enamelin-amelogenin ratio of about 1:10, in the presence of a catalytically effective amount of a serine protease at a temperature of about 37° C. and a pH of from about 7.2 to about 8.1 which results in the formation of dental enamel crystals.

5. The method of claim 4 wherein said solution is supersaturated with calcium phosphate.

6. The method of claim 4 or 5 wherein the solution further includes at least 5 ppm fluoride.

* * * * *